United States Patent [19]

West, Jr.

[11] Patent Number: 5,364,395
[45] Date of Patent: Nov. 15, 1994

[54] ARTHROSCOPIC SURGICAL INSTRUMENT WITH CAUTERIZING CAPABILITY

[76] Inventor: Hugh S. West, Jr., 1373 Harvard Ave., Salt Lake City, Utah 84105

[21] Appl. No.: 62,349

[22] Filed: May 14, 1993

[51] Int. Cl.$^5$ .............................................. A61B 17/32
[52] U.S. Cl. ...................................... 606/46; 606/49; 606/170; 604/22
[58] Field of Search ................... 607/115, 116; 606/41, 606/45, 46, 49, 170, 180; 604/21, 22

[56] References Cited

U.S. PATENT DOCUMENTS

| | | |
|---|---|---|
| 3,828,780 | 8/1974 | Morrison, Jr. . |
| 3,945,375 | 3/1976 | Banko ................................. 606/49 |
| 4,815,462 | 3/1989 | Clark . |
| 4,850,354 | 7/1989 | McGurk-Burleson et al. . |

Primary Examiner—Stephen C. Pellegrino
Assistant Examiner—Michael Peffley
Attorney, Agent, or Firm—Workman Hydegger Jensen

[57] ABSTRACT

An instrument capable of selectively cutting or cauterizing tissue includes a handle and an elongated electrically conductive probe with a longitudinally extending lumen communicating with the handle. The distal end of the probe has an aperture formed therethrough between the lumen and the exterior of the probe. An elongated drive shaft is disposed within the lumen for rotation about the longitudinal axis of the drive shaft. A cutting tool is positioned on the shaft opposite the aperture. An electrically insulative layer is disposed on the exterior of the probe extending from the proximal end of the probe to the periphery of a preselected region on the distal end of the probe. The preselected region is selectively couplable to a power source to permit cauterization. An alternate embodiment employs an electrically insulative probe and an embedded electrically conductive pathway coupled to the preselected region. Yet another embodiment utilizes an electrically insulative sleeve selectively disposable about the exterior of the probe. An electrocautery contact is exposed at the outer surface of the distal end of the sleeve and is electrically coupled through the probe, or through an electrical pathway embedded in the sleeve, in order the couple the contact to a power source.

53 Claims, 13 Drawing Sheets

ARTHROSCOPIC SURGICAL INSTRUMENT WITH CAUTERIZING CAPABILITY

BACKGROUND

1. The Field of the Invention

The present invention relates generally to an arthroscopic surgical instrument. More specifically, the present invention relates to a surgical instrument utilizing an electrical power source in a surgical procedure to cut tissue of a patient at an internally located surgical site, while selectively controlling bleeding of the patient at that surgical site.

2. Background Art

Arthroscopy is an increasingly commonplace surgical procedure. The inherent advantage to arthroscopy is that the procedure is associated with relatively short patient recovery periods and minimal scarring. What were historically considered to be fairly complex surgeries with lengthy recovery periods, have, through the use of arthroscopy, become outpatient procedures.

The ability to perform surgery on an outpatient basis greatly reduces the cost of surgery. An associated reduction in cost is the absence of the usually necessary pre-operative and post-operative hospital stay for the patient. For this reason, arthroscopy, which was previously limited to knee and shoulder surgery, is now spreading into other areas previously reserved for more traditional methods of surgery.

A. The Arthroscope and Surgical Cutting Tools

An arthroscope is an instrument used to look directly into a surgical site through a first incision thereto. The ability to view the surgical site in this manner allows for a minimally invasive procedure, that is useful in both diagnosis and treatment. Typically, the arthroscope utilizes a magnifying lens and coated glass fibers that beam an intense, cool light into the surgical site. A camera attached to the arthroscope allows the surgeon to view the surgical site through other optical fibers on a monitor in the operating room.

While viewing the surgical site with the arthroscope, the surgeon performs any necessary repair and reconstruction by using a separate surgical instrument that is inserted through a second incision to the surgical site. The surgical instrument is capable of utilizing different cutting tools to sever tissue.

Such cutting tools can include a rotating, straight edge blade that incises tissue that it contacts. Serrated blades can also be used to effect the cutting of tougher tissue. Cutting blades, whether straight or serrated, are used to sever the tissue of a patient. Burrs, which are often conical or orbed blades with projecting cutting edges, can be utilized for shaving or grinding the tissue of a patient. A burr can also be used to stimulate cartilage growth or shave away damaged cartilage at the surgical site.

Generally, a surgical instrument of this type includes a hollow probe with an aperture formed therethrough, generally at or near the distal tip. A rotatable drive shaft is longitudinally disposed within the hollow probe. A cutting tool is positioned on the drive shaft so that when the drive shaft is inserted within the probe, the cutting tool is opposite the aperture. When the cutting tool is urged against tissue of the patient, the cutting tool shaves or severs tissue of the patient.

B. The Arthroscopic Procedure

With the arthroscope, the surgeon can look directly into the surgical site, usually the knee or shoulder, to diagnose injury and decide on the best treatment. At the beginning of the arthroscopic procedure, the patient receives an anesthetic. The anesthetic may be administered generally, regionally, or locally. General anesthetic will completely anesthetize the patient. Regional anesthesia will numb the patient from the waist down and is called spinal anesthesia. Local anesthesia reduces the sensitivity at the specific locale of surgery, but allows the patient to remain conscious throughout the surgical procedure.

After the patient has been sufficiently anesthetized, the surgeon makes a plurality of incisions, known as portals, from the exterior of the body of the patient to the surgical site. Three portals are usually made: a first for the arthroscope, a second for the surgical instrument, and a third to permit fluids to escape from the surgical site.

Sterile fluid is generally introduced by way of the arthroscope through the first portal. The sterile fluid serves among other purposes to expand the area of the surgical site. The insertion of sterile fluid makes it easier to see and work inside the body of the patient at the surgical site. The arthroscope is inserted also through the first portal to allow the surgeon to confirm the type and degree of damage. Surgical instruments can then be inserted through the second portal to, generally, either shave or sever tissue at the surgical site.

During the procedure of cutting or shaving, the debridement of tissue can frequently cause bleeding into the surgical site. Such bleeding immediately obscures the viewing field of the arthroscope. Bleeding is more severe when a tourniquet is not or cannot be utilized. For example, when performing arthroscopic surgery in the shoulder, the physical location of the shoulder relative to the rest of the body and the arteries feeding blood to the shoulder makes it impractical to use a tourniquet to control bleeding. Therefore, significant bleeding is usually expected in surgery in the shoulder.

In order to control such bleeding at the surgical site, it is necessary to remove the surgical instrument completely from its associated portal and reinsert an electrocautery probe through the same portal. The electrocautery probe can be selectively electrically energized.

In electrocautery, the body of the patient is grounded, and the tip of the energized electrocautery probe is brought to bear against the tissue of the patient at any open blood vessel. A high frequency electrical current flows from the probe through the tissue of the patient at that point. That tissue, including any open blood vessels therein, is heated by the current, coagulating the tissue and sealing the open ends of the blood vessels. The blood produced prior to sealing off of the blood vessel is then removed from the surgical site by the continuous flow of the sterile fluid through the surgical site. This restores visibility in the surgical site. Then the cauterizing to:31 is removed, the surgical tool reinserted, and surgery is resumed.

Removal of the surgical instrument when bleeding is detected and the subsequent insertion of the electrocautery probe through the same portal in combination with its removal after cauterization has occurred and the reinsertion of the surgical instrument is an arduous task. During the period of time between when the surgical instrument is removed and the electrocautery probe is inserted, a significant amount of blood can accumulate at the surgical site and make it difficult to visually locate the actual source of the bleeding. Moreover, the process of removing the surgical instrument, inserting the electrocautery probe, .and reinserting the surgical instrument consumes time, extending the duration of the surgery. The use of separate tools to cauterize and perform surgery increases the overall cost of the surgical procedure.

Additionally, the use of a tourniquet to control bleeding at the surgical site has received increased criticism because numerous studies have demonstrated that use of a tourniquet increases morbidity. The most notable post-operative complication from use of a tourniquet is hemarthrosis. Hemarthrosis involves blood discharging or escaping blood and accumulating at the surgical site following the completion of the surgical procedure.

OBJECTS AND SUMMARY OF THE INVENTION

Accordingly, it is an object of the present invention to provide a surgical instrument that reduces the overall cost of surgical procedures.

Another object of the present invention is to provide an arthroscopic surgical instrument with cauterizing capability, thereby to allow arthroscopic surgery to occur where use of a tourniquet is impractical or undesirable.

Yet another object of the present invention is to provide an arthroscopic surgical instrument with cauterizing capability that does not require the use of a tourniquet since bleeding could be efficiently and quickly controlled, thus reducing any morbidity arising from use of a tourniquet.

It is also an object of the present invention to provide an arthroscopic surgical instrument with cauterizing capability that reduces the difficulty arising from the need to quell bleeding at a surgical site by removing the surgical instrument, inserting an electrocautery probe to cauterize the blood vessel, removing the electrocautery probe, and reinserting the surgical instrument in order to continue the operation.

It is another object of the present invention to provide an arthroscopic surgical instrument with cauterizing capability that reduces the time consumed in surgery associated with discovering bleeding at the surgical site.

Another object of the present invention is to provide an arthroscopic surgical instrument with cauterizing capability which obviates the need to resort to multiple instruments for surgery and cauterization.

It is also an object of the present invention to provide an arthroscopic surgical instrument with cauterizing capability that quickly and efficiently controls bleeding at the surgical site, so that the view of the surgeon is not obscured when an arthroscope is utilized.

Still another object of the present invention is to provide an arthroscopic surgical instrument with cauterizing capability whereby the surgeon can promptly find and cauterize the source of bleeding.

Another object of the present invention is to provide an arthroscopic surgical instrument which is capable of mechanically cutting the tissue of the patient and cauterizing on a selective basis. Another object of the present invention is to provide an arthroscopic surgical instrument which is capable of electro-surgically cutting the tissue of the patient on a selective basis.

Additional objects and advantages of the invention will be set forth in the description that follows, and in part will be obvious from the description or may be learned by the practice of the invention. The objects and advantages of the invention may be realized and obtained by means of the instruments and combinations particularly pointed out in the appended claims.

To achieve the foregoing objects, in accordance with the invention as embodied and broadly described herein, an instrument is provided for use with an electrical power source and a surgical procedure to cut tissue of a patient. The instrument comprises a handle and an elongated electrically conductive probe. The probe has a proximal end and a distal end and is attached to the handle at the proximal end.

The probe is formed so that a longitudinally extending lumen is disposed in the interior thereof and the lumen communicates with the handle. The distal end of the probe has an aperture for permitting the lumen of the probe to communicate with the exterior of the probe. The instrument further comprises an elongated drive shaft longitudinally disposed within the lumen extending from the proximal end of the probe to at least the aperture formed in the probe. The shaft is rotatable about its longitudinal axis within the lumen.

Additionally, the instrument comprises a cutting tool positioned on the drive shaft opposite the aperture. The cutting tool passes in close proximity to the aperture during each rotation of the drive shaft. In this manner, the tissue of the patient may be severed which is urged against the exterior of the probe at the aperture.

Versatility means are further provided for selectively electrically cauterizing tissue of the patient contacting a preselected region on the exterior of the distal end of the probe. By way of example and not limitation, the versatility means comprises an electrically insulative layer disposed on the exterior of the probe. The layer extends from the proximal end of the probe to the periphery bounding the preselected region. The versatility means is further comprised of an energization means for effecting selective electrical coupling of the probe with the power source.

By way of example and not limitation, an energization means is utilizable with the present invention and comprises a cable having a first end and a second end. The first end is couplable to the power source and a switch is secured to the proximal end of the probe. The switch is also electrically coupled to the second end of the cable. In this manner the cable and the proximal end of the probe may be selectively electrically coupled.

One embodiment of the present invention contemplates that the preselected region is formed as a protuberance projecting from the distal end of the probe. In another embodiment of the present invention, the protuberance is projected from the distal end of the probe in a direction normal to the longitudinal axis of the probe. The protuberance may also be disposed so that the tip of the protuberance is further from the longitudinal axis of the probe than the exterior of the layer.

In another embodiment of the present invention the probe comprises conductive means electrically coupling the preselected region to the proximal end of the probe, and electrically insulated from the exterior of the probe.

Still another embodiment of the present invention contemplates the conductive means being electrically insulated from the interior of the probe. The conductive means may comprise an electrically conductive ribbon embedded in the wall of the probe that could be formed by injection molding.

Another embodiment of the present invention contemplates an electrically insulated sleeve selectively disposable about the exterior of a non-insulated probe. In this embodiment, the sleeve extends from the proximal end of the probe to the distal end. The sleeve also has a first end and a second end. The first end and the second end are positioned so as to be adjacent to the proximal end and the distal end of the probe, respectively, when the sleeve is disposed above the exterior of the probe.

The second end of the sleeve has an aperture. The aperture is positioned on the exterior of the probe to permit the lumen of the probe to communicate with the exterior of the sleeve. The instrument is further comprised of an electrically conductive preselected region located on the exterior of the second end of the sleeve that functions, and will be referred to hereinafter, as an electrocautery contact. Securing means is also provided for attaching the sleeve at the first end to the handle and energization means is attached to the sleeve for permitting the preselected region to be selectively electrically coupled with the power source.

In another embodiment of the present invention the energization means attached to the sleeve for permitting the electrocautery contact to be selectively electrically coupled with the power source comprises a cable having a first end and a second end. The first end is couplable to the power source and a switch is secured to the proximal end of the sleeve. The switch is also electrically coupled to the second end of the cable. Conductive means conductive pathway is disposed on the interior of the sleeve to electrically couple the electrocautery contact to the proximal end of the probe.

In still another embodiment of the present invention the conductive means is embedded within the sleeve.

The claimed invention also contemplates a method for conducting a surgical procedure to cut tissue of a patient located at a surgical site interior to the body of patient, while electrically controlling bleeding at the surgical site. The method comprises the steps of forming a passageway from the exterior of the body of the patient to the surgical site. The tip of a surgical instrument constructed according to the teachings of the present invention is advanced through the passageway to the surgical site. The method therefore further comprises the steps of electrically insulating the exterior of the probe from the proximal end to an edge bounding a preselected region of the exterior of the distal end of the probe.

The surgical site is visually observed during use of the instrument to cut the tissue of the patient. The electrical power source is electrically coupled to the proximal end of the probe when bleeding at the surgical site is detected in the step of visually observing. Thus, the preselected region on the exterior of the distal end of the probe is allowed to cauterize tissue of the patient contacted thereby, and the step of electrically coupling is terminated when the step of visually observing discloses that bleeding at the surgical site has been curtailed by cauterizing the tissue of the patient.

Alternative methods of performing the step of electrically insulating may comprise the step of sliding an electrically insulated sleeve onto the exterior of the probe until the first end of the sleeve is into abutment with the handle, and aligning the aperture of the probe with the aperture of the second end of the sleeve to permit the lumen of the probe to communicate with the exterior of the sleeve. Another method of electrically insulating comprises the step of sliding an electrically insulated heat shrinkable cylinder onto the exterior of the probe and into abutment with the handle. The electrically insulated cylinder is configured to extend from the handle to an edge bounding the preselected region on the exterior of the distal end of the probe. The cylinder is then heated to shrink the cylinder into tight engagement with the exterior of the probe.

Still, another alternative method of performing the step of electrically insulating may comprise the steps of masking the preselected region on the exterior of the probe and masking the aperture formed through the distal end of the probe. The probe is then immersed into a liquified insulative material and the insulative material is cured. The masking is then removed from the preselected region of the probe and from the aperture.

Yet another alternative method of performing the step of electrically insulating comprises the steps of applying an adhesive to the exterior of the probe from the proximal end to the edge bounding the preselected region and advancing an electrically insulative sleeve onto the exterior of the probe in contact with the adhesive. The adhesive is then cured to bond the electrically insulative layer to the exterior of the probe.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof, which is illustrated in the appended drawings and which constitutes the best mode presently contemplated with respect to the invention.

Understanding that these drawings depict only typical embodiments of the invention and are not, therefore, to be considered limiting of its scope, the invention will be described with additional specificity and detail through the use of the accompanying drawings in which.

DETAILED DESCRIPTION OF THE PREFERRED EMBODIMENT

Figure 1:
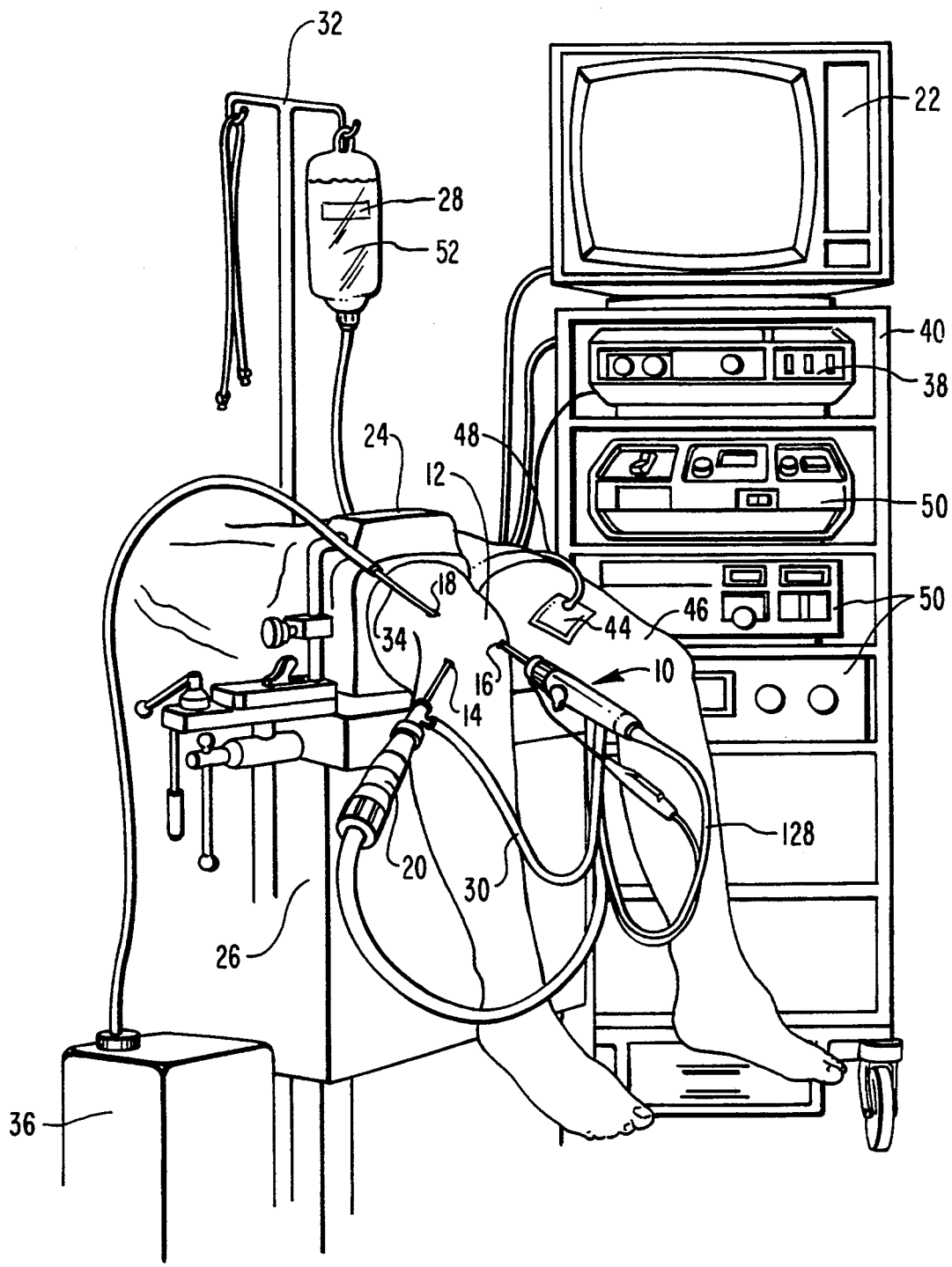
FIG. 1 is a perspective view of an operating room where surgery is being conducted on the knee of a patient with an instrument incorporating the teachings of the present invention.

FIG. 1 is a perspective view of an operating room where surgery is being conducted on the knee of a patient with an instrument 10 incorporating the teachings of the present invention. There, knee 12 is shown with arthroscope portal 14, instrument portal 16 and suction portal 18 created therein. It is contemplated that the present invention is used in connection with arthroscope 20, which is inserted in arthroscope portal 14 that was created on the exterior of knee 12 and extended to a surgical site.

As used herein, the term "surgical site" includes any location in the body of a patient at which surgery is performed. Thus, although knees and shoulders have been discussed as possible surgical sites, the term surgical sites as used in this context includes any location relating in the body of a patient at which surgery is performed. Moreover, although it is contemplated that the present invention will be used with an arthroscope, the present invention is not solely limited to that procedure. Thus, the present invention could be used above, in connection with instruments performing functions like that of an arthroscope or instruments slightly related or totally unrelated to an arthroscope, and the location of the surgical procedure undertaken thereby would be within the meaning of the term surgical site as used herein, a instrument incorporating the teachings of the present invention is utilized in a procedure.

The individual performing the surgical procedure is capable of viewing the surgical site within knee 12 on monitor 22 by use of an arthroscope 20. In order to restrain knee 12 from unnecessary movement during the surgical procedure, a brace 24 is secured to an operating table 26 upon which the patient is disposed. Knee 12 is then clamped to operating table 26 by brace 24.

During the operation, a sterile fluid 52 contained in a bag 28 passes through a sterile fluid tube 30 and into the surgical site through passageways built into arthroscope 20. Bag 28 is normally positioned on a stand 32 to provide optimal head pressure for sterile fluid 52 relative to knee 12. A suction tube 34 is inserted through suction portal 18 until the distal end of suction tube 34 reaches the surgical site. Suction tube 34 can then be used to drain excess fluid from the surgical site for deposit in a waste fluid container 36. Waste fluid container 36 is positioned at a lower height relative to knee 12 to allow excess fluid to be drained through suction tube 34 without additional need for equipment.

Instrument 10 is inserted through instrument portal 16 to the surgical site and used to perform the necessary repair or reconstruction inside knee 12. The nature and extent of the repair or reconstruction is determined after viewing the surgical site on monitor 22 through arthroscope 20. As shown in FIG. 1, instrument 10 is coupled to a power source 38 that resides on a stand 40. Instrument 10 is also connected to a vacuum source of suction for storage by way of a closed fluid system in a receiving container similar to waste fluid container 36.

A grounding patch 44 is positioned on leg 46 to permit any current from instrument 10 to escape the body of the patient upon cauterization. This is accomplished by attaching grounding patch 44 to a conductive wire 48, which is grounded on an appropriate structure in the operating room. Other instruments 50 positioned on stand 40 are also depicted in FIG. 1, which may be useful during the surgical procedure.

Figure 2:
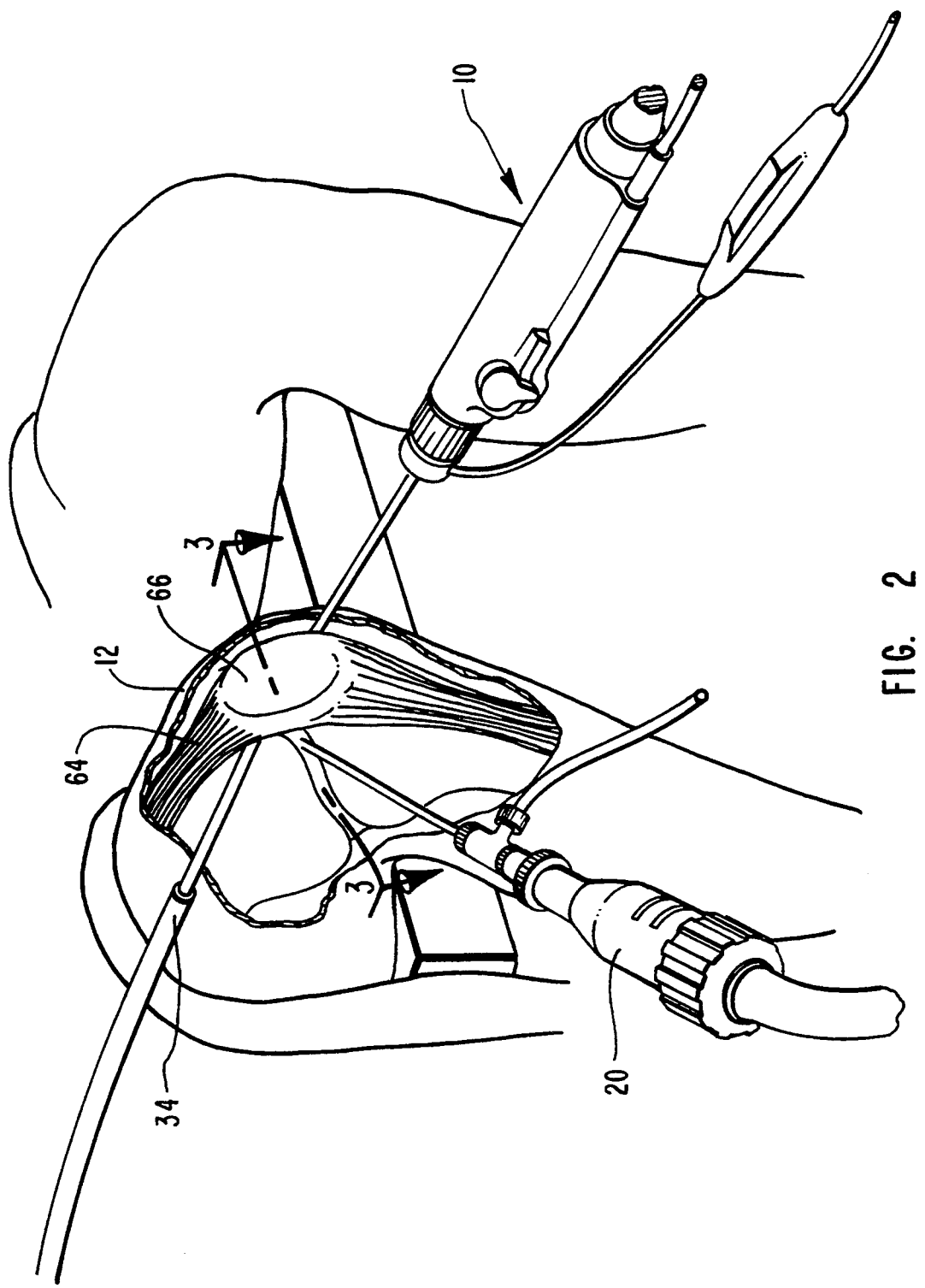
FIG. 2 is an enlarged view of FIG. 1 with the knee partially exposed and an instrument incorporating the teachings of the present invention, as well as other tools associated with the procedure illustrated, are inserted behind the patella tendon and the patella.

FIG. 2 is an enlarged view of FIG. 1 with some of the internal structures of knee 12 partially exposed, and with instrument 10, which incorporates the teachings of the present invention, inserted behind the patella tendon 64 and the patella 66 of the patent. Also shown in FIG. 2 is arthroscope 20 positioned behind patella tendon 64 and patella 66, and suction tube 34 positioned at a location sufficient to allow suction of excess fluids to occur.

When inserting arthroscope 20 through arthroscope portal 14 and instrument 10 through instrument portal 16, insertion should be made such that an angle of insertion allows the individual performing the surgical procedure the optimal viewing area along with the optimal position for free movement of instrument 10 to permit the operation to occur without hinderance.

Figure 3:
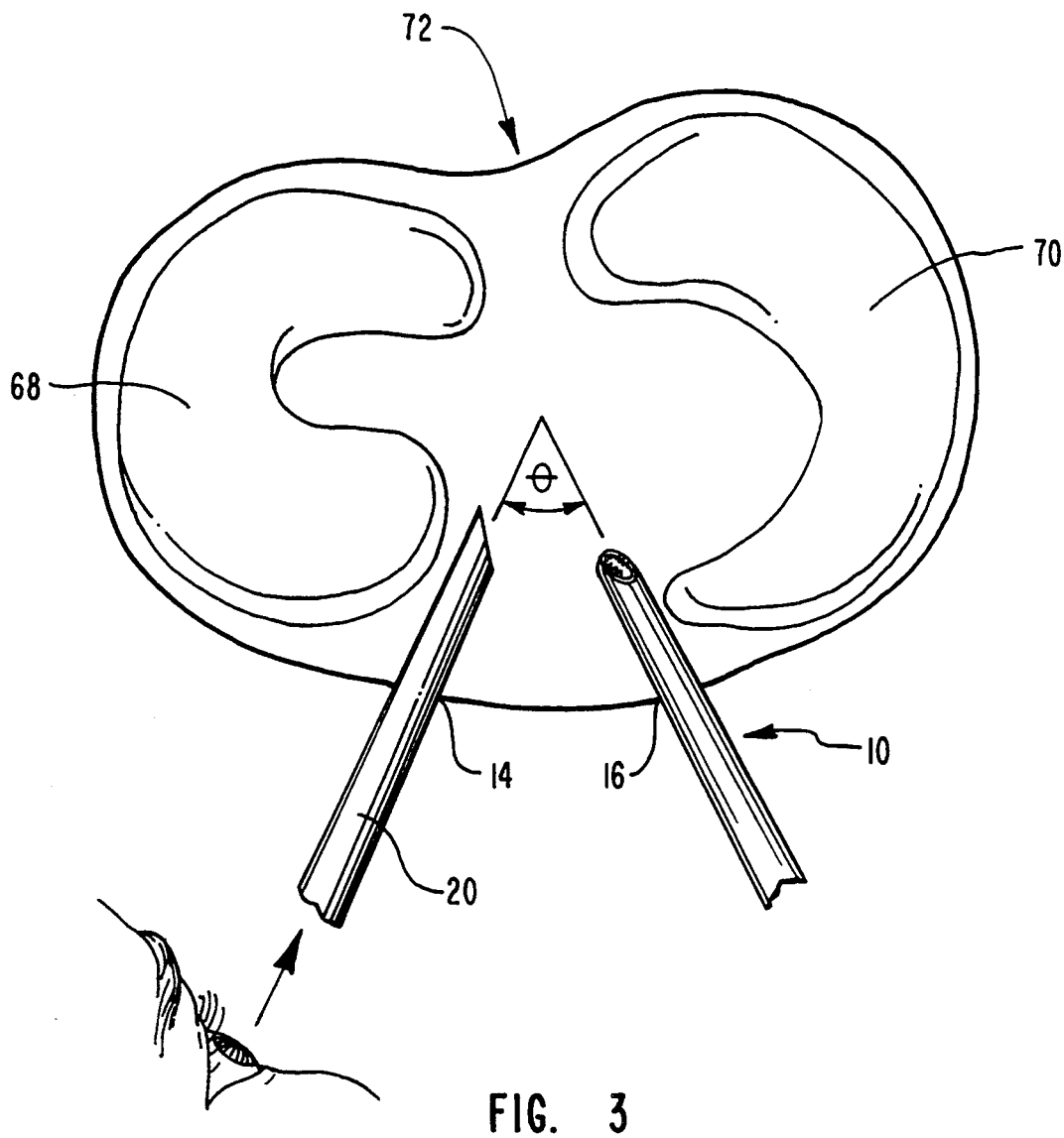
FIG. 3 is a plan view of the knee of the patent taken along line 3—3 in FIG. 2 illustrating the angle of insertion of the arthroscope relative to the instrument incorporating teachings of the present invention and the lateral meniscus and medial meniscus.

As further depicted in FIG. 3, arthroscope 20 is inserted through arthroscope portal 14. Upon discovering that injury necessary of repair or reconstruction has occurred, the individual performing the surgical procedure can then insert instrument 10 through instrument portal 16 at an angle Θ shown in FIG. 3, relative to arthroscope 20. Preferably angle Θ is 90° or less. In this manner, the individual performing the procedure can view the widest angle in surgical site 72 without obstructing the viewing area of arthroscope 20. Arthroscope 20 and instrument 10 may be inserted between lateral meniscus 68 and medial meniscus 70, to permit the necessary repair or reconstruction without excess hinderance of movement.

Figure 4:
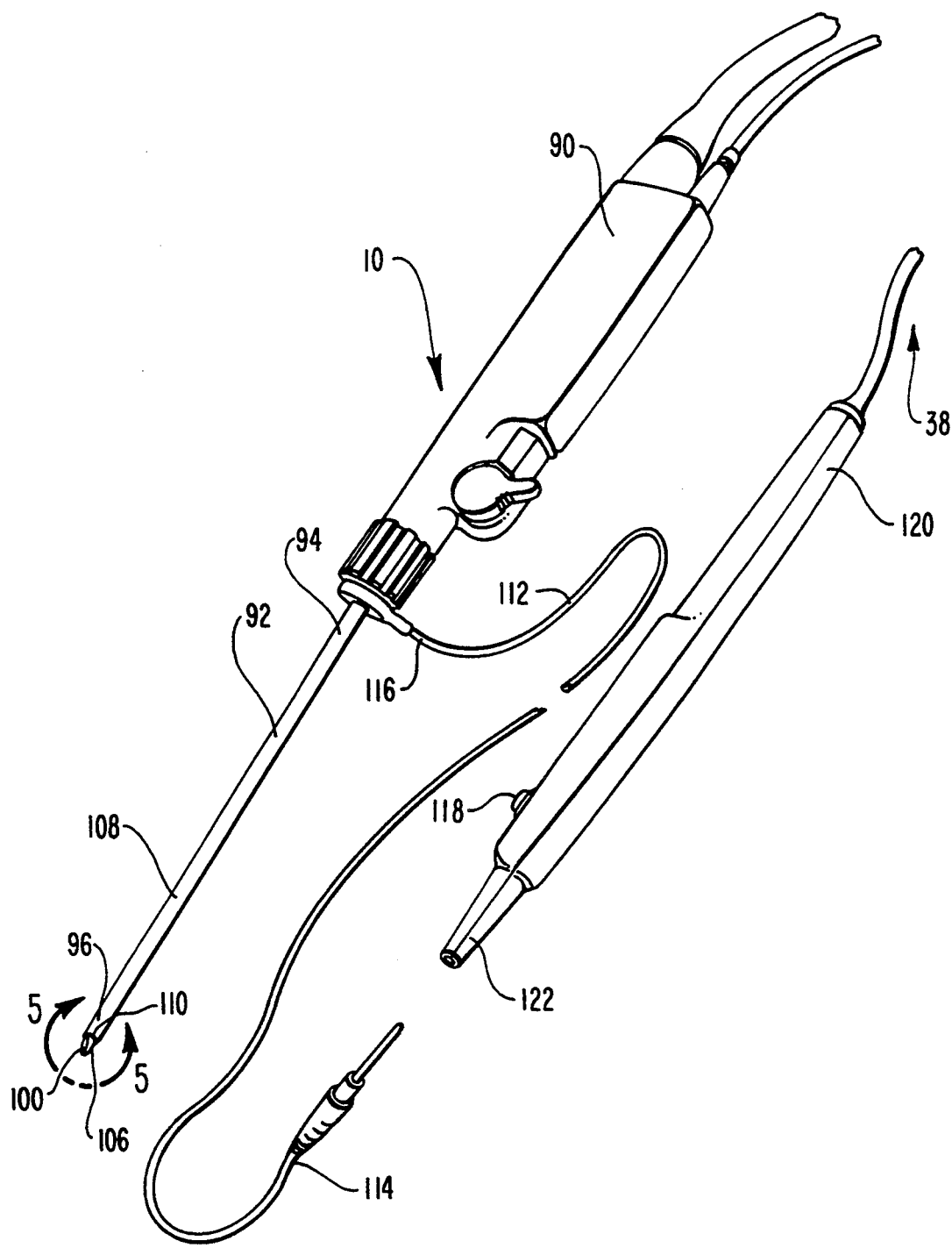
FIG. 4 is a perspective view of the inventive instrument of FIG. 1 removed from the knee.

As shown in FIG. 4, a presently preferred embodiment of instrument 10 is provided for performing such repair or reconstruction utilizing an electrical power source that is capable of selectively electrically cauterizing. Instrument 10 comprises a handle 90 and an elongated electrically conductive probe 92 that has a proximal end 94 and a distal end 96. Probe 92 is attached at proximal end 94 thereof to handle 90.

Probe 92 has formed in the interior thereof a longitudinally extending lumen 98 (See FIG. 6) communicating with handle 90. Distal end 96 of probe 92 has formed therethrough aperture 100 that permits lumen 98 to communicate with the exterior of probe 92.

Instrument 10 further comprises an elongated drive shaft 102 (See FIG. 6) longitudinally disposed within lumen 98, extending from proximal end 94 of probe 92 to at least aperture 100. Shaft 102 is rotatable about its longitudinal axis within lumen 98. Instrument 10 further comprises cutting tool 104 (See FIG. 5) positioned on shaft 102 opposite aperture 100, so as to pass in close proximity thereto during each rotation of shaft 102. In this manner, any tissue of the patient urged against the exterior of probe 92 at aperture 100 is severed as cutting tool 104 passes by aperture 100.

As used herein the term "cutting tool" is intended to include any device suitable for severing, shaving, grinding, or altering tissue of a patient. Moreover, other devices may be suitable for performing these procedures with an instrument incorporating the teachings of the present invention. That portion of such other devices is intended to be included in the term cutting tool whether incising, tearing or performing repair of reconstruction relative to a patient, whether or not tissue is involved.

The above identified structures assist in allowing the inventive device to perform repair or reconstruction by use of a cutting tool. The inventive device, however, is further capable of also functioning to cauterize as needed when determined by observation. Toward that end, distal end 96 of probe 92 includes a preselected region that effects cauterization on a selected basis when tissue of a patient is urged against such preselected region.

Instrument 10 further comprises versatility means for selectively electrically cauterizing tissue of a patient contacting a preselected region on the exterior of the distal end of probe 92. By way of example and not limitation an example of one such versatility means is shown in FIG. 4, to comprise an electrically insulative layer 108 disposed on the exterior of probe 92. Insulative layer 108 extends from proximal end 94 of probe 92 to the periphery 110 bounding preselected region 106 on the exterior proximal of distal end 96 of probe 92.

Preselected region 106 may be of any shape or size desired so long as preselected region 106 is formed to permit effective cauterization. Thus, by way of example and not limitation, preselected region 106 could project from probe 92, could be flush with insulative layer 108, or could comprise the entire tip or a portion of the tip of distal end 96.

The versatility means used in the inventive device further comprises energization means for effecting selective electrical coupling of probe 92 with power source 38 shown in FIG. 1.

Because of the electrical charge from power source 38 passing through instrument 10, versatility means is capable of cutting tissue of a patient and is also capable of providing hemostasis in the patient. The present invention then possesses dual cutting capabilities. Cutting of tissue can occur mechanically by use of a cutting tool. Also, cutting of tissue can occur electro-surgically by use of versatility means. The electro-surgical cutting ability of the present invention is capable of being used in lieu of the cutting tool or complimentary with the cutting tool. Therefore, where tissue of a patient is difficult to sever by use of the cutting tool, versatility means may be employed to perform medical repair or reconstruction.

As shown in FIG. 4, energization means, by way of example and not limitation, comprises cable 112 having first end 114 and second end 116. Second end 116 of cable 112 is secured to probe 92 at proximal end 94 such that cable 112 is capable of being electrically coupled to proximal end 94 of probe 92. First end 114 of cable 112 is selectively electrically couplable at first end 114 with electrical power source 38. In this embodiment, power source 38 is electrically couplable to switch 118 at second end 120, and switch 118 is electrically couplable at first end 122 with first end 114 of cable 112. In this manner, instrument 10 is capable of being used without permanently maintaining electrical coupling with power source 38 if so desired.

Figure 5:
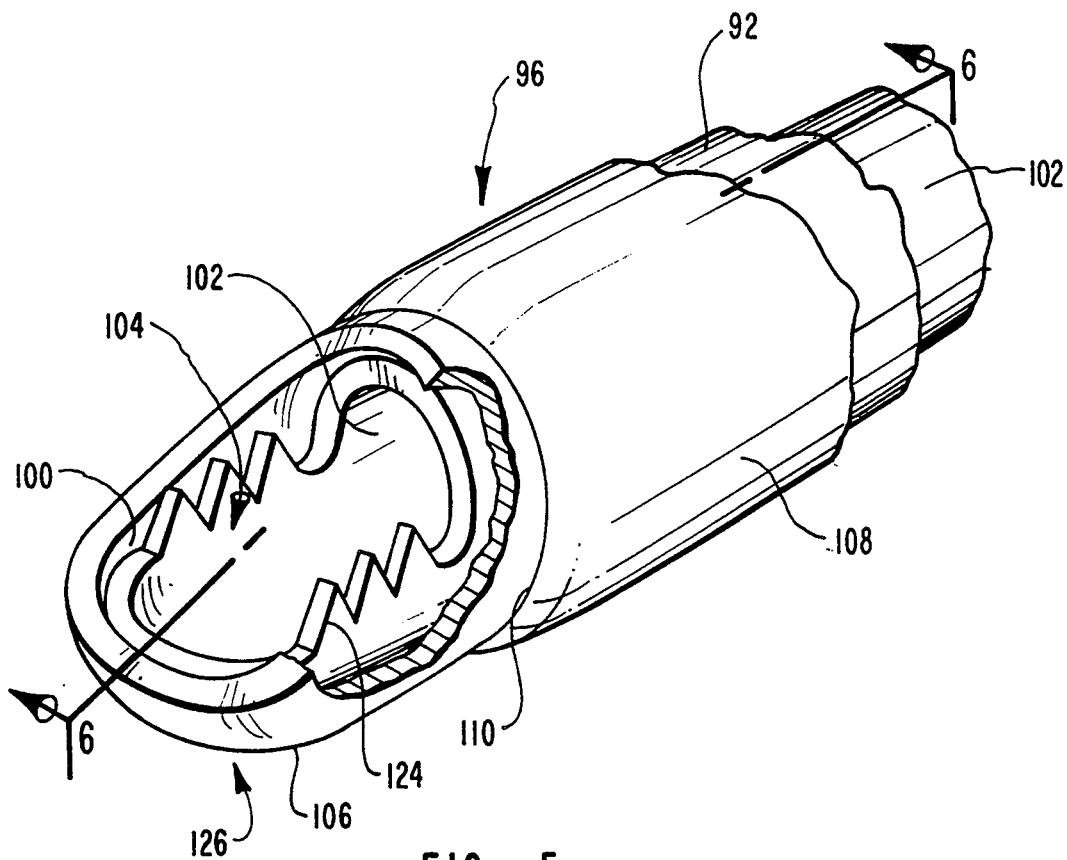
FIG. 5 is an enlarged detail view of the portion of distal end of the inventive instrument encircled by line 5—5 in FIG. 4.

FIG. 5 is an enlarged detailed view of distal end 96 of probe 92. The enlarged view of distal end 96 depicts cutting tool 104 as serrated blade 124. As can be seen from FIG. 5, periphery 110 bounding preselected region 106 may be formed in a bevel shape to avoid any unnecessary tearing of tissue of the patient when probe 92 is inserted through instrument portal 16 or utilized during the procedure.

As depicted in FIG. 5, probe 92 may have a substantially circular cross section. In this instance, periphery 110 comprises a circle perpendicular to the longitudinal axis of probe 92. Also as seen in FIG. 5, preselected region 106 may comprise tip 126 of distal end 96.

Figure 6:
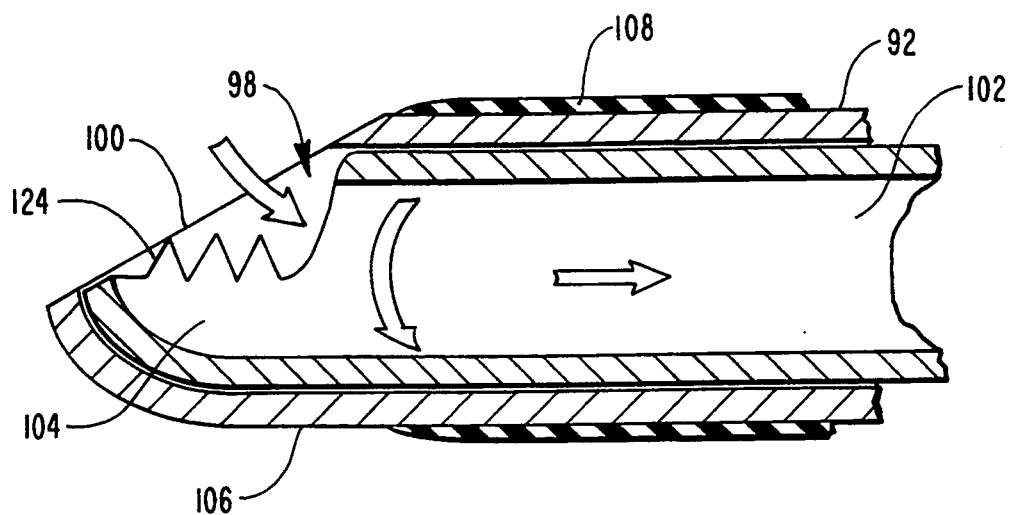
FIG. 6 is a longitudinal cross-sectional view of the distal end of the inventive instrument taken along line 6—6 in FIG. 5.

FIG. 6 is a longitudinal cross-sectional view of the distal end of instrument 10 in FIG. 5 and depicts the position of shaft 102 with respect to lumen 98 of probe 92. As is also demonstrated in FIG. 6, shaft 102 extends to at least aperture 100. As shaft 102 rotates about its longitudinal axis within lumen 98, any tissue severed by cutting blade 104 may be drawn down the interior of shaft 102 by use of suitable suction instrument. Any tissue passing through shaft 102 can then be deposited in a suitable container without probe 92 by use of tubing 128 and suction equipment 42.

Figure 7:
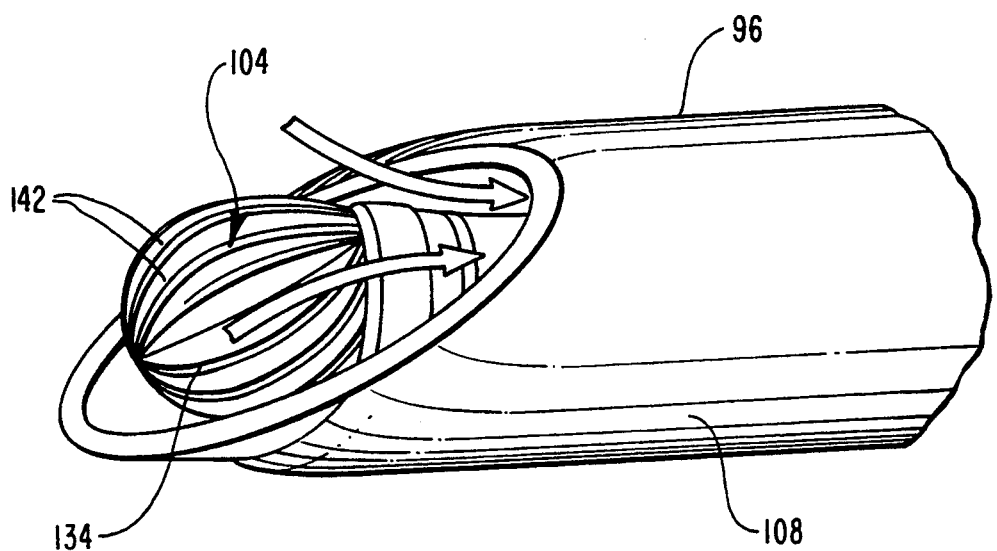
FIG. 7 is a perspective view of the distal end of an alternative embodiment of an instrument incorporating the teachings of the present invention and using a burr as the cutting tool.

Cutting tool 104 may further comprise burr 134 as seen in FIG. 7. As used herein, the term "burr" includes any shaped instrument that performs the procedure of grinding, shaving or tearing. As seen in FIG. 7, burr 134 may be orbitally formed. Burr 134 may also be conical or some other shape. Most burrs contain multiple protruding edges 142. However, protruding edges 142 may be unnecessary so long as burr 134 is formed as to effectively assist in the process of grinding, shaving or tearing.

Figure 8:
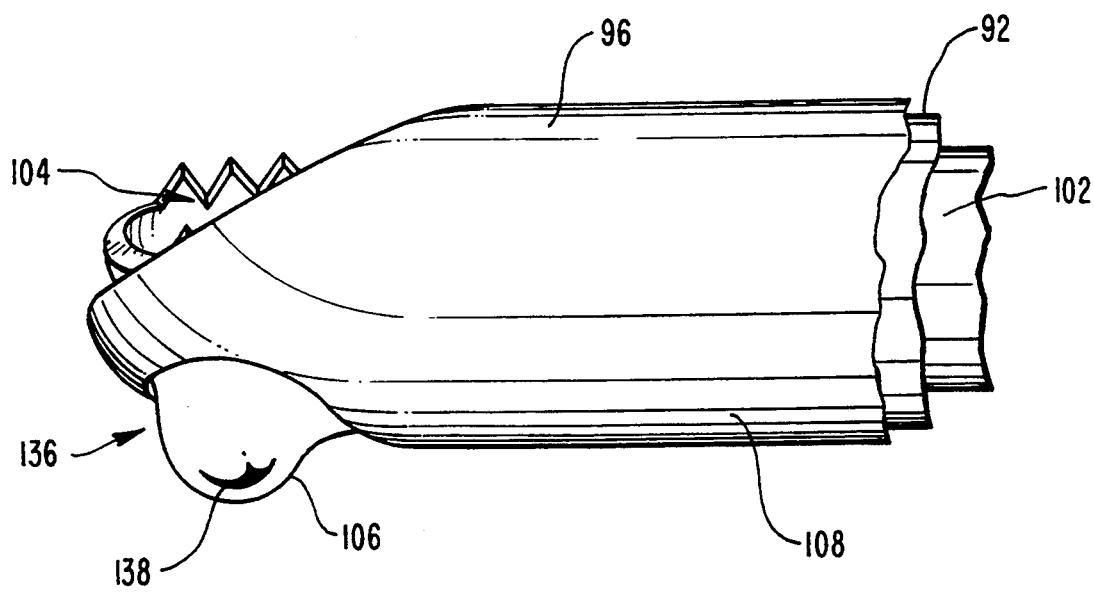
FIG. 8 is a perspective view of the distal end of another alternative embodiment of an instrument incorporating the teachings of the present invention using a serrated blade as the cutting tool and a protuberance as the preselected region for effecting cauterization.

FIG. 8 shows distal end 96 of probe 92 in another embodiment of an instrument incorporating the teachings of the present invention. In such embodiment preselected region 106 comprises protuberance 136 projecting from distal end 96 of probe 92. An embodiment of the present invention contemplates protuberance 136 projecting from distal end 96 in a direction normal to the longitudinal axis of probe 92. In another embodiment, protuberance 136 projects from distal end 96 of probe 92 in a direction normal to the longitudinal axis of probe 92 and protuberance 136 has tip 138 disposed further from the longitudinal axis from probe 92 than the exterior of insulative layer 108.

Insulative layer 108 comprises in one embodiment of the present invention a heat shrinkable material. Such a material is disposed about the exterior of probe 92 in tight engagement with the exterior of probe 92. Insulative layer 108 may also be adhesively attached to the exterior of probe 92. Additionally, insulative layer 108 may also be applied to the exterior of probe 92 by immersing probe 92 in a liquid material which may be cured to form insulative layer 108.

Figure 9:
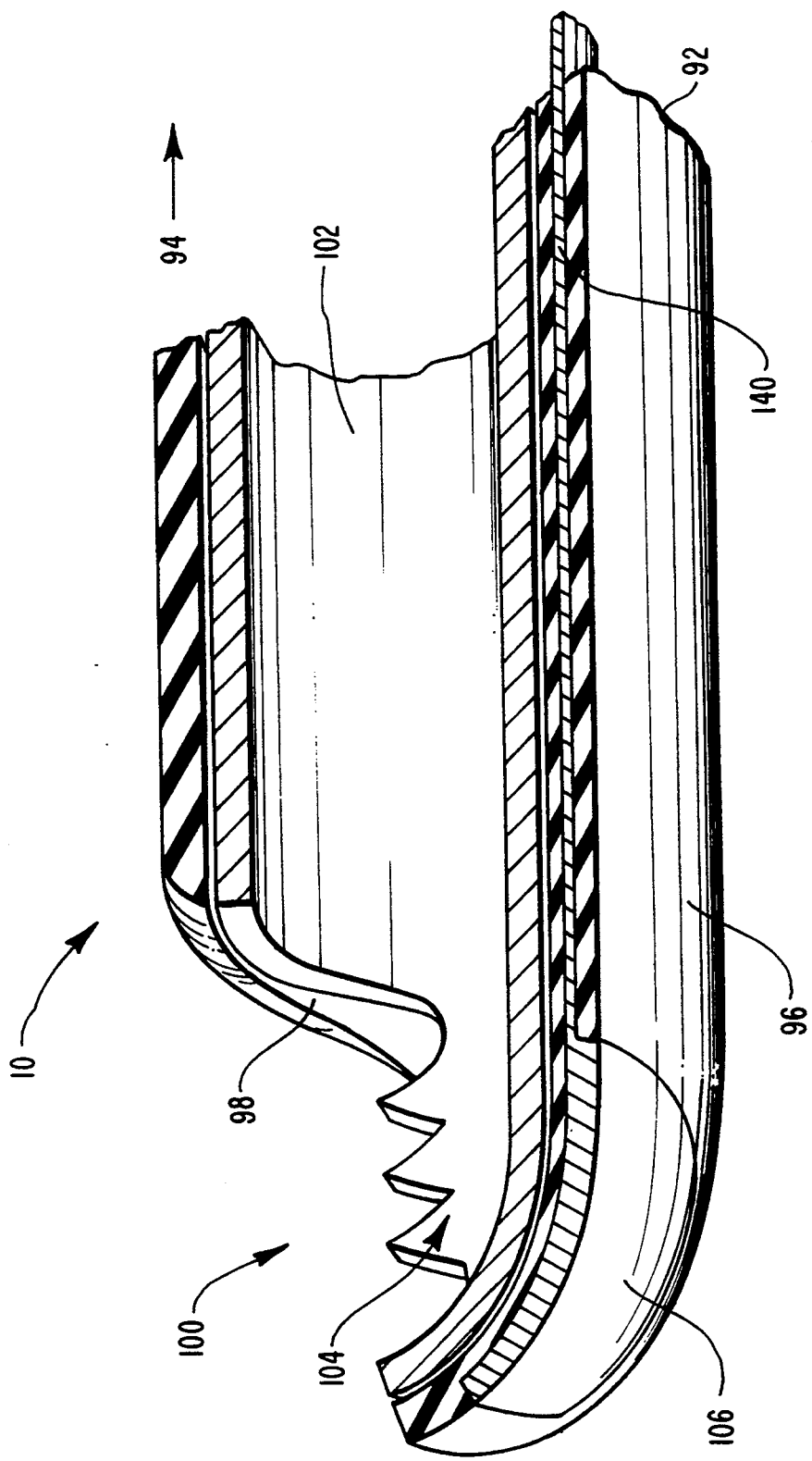
FIG. 9 is a longitudinal cross-sectional view of the distal end of yet another alternative embodiment of an instrument incorporating the teachings of the present invention in which the probe is electrically nonconductive and an electrical pathway is embedded in the wall of the probe.

Another embodiment of an instrument incorporating the teachings of the present invention is shown in FIG. 9. Such embodiment comprises handle 90 not unlike that depicted in FIG. 4. Instrument 10 further comprises an elongated probe 92 having proximal end 94 and distal end 96. Probe 92 is attached at proximal end 94 to handle 90. Probe 92 has formed in the interior thereof a longitudinally extending lumen 98 communicating with handle 90. Distal end 96 of probe 92 has aperture 100 formed through probe 92 permitting lumen 98 to communicate with the exterior of probe 92.

Probe 92 further comprises an electrically conductive preselected region 106 located on the exterior of distal end 96 of probe 92. Probe 92 further comprises an electrically conductive pathway 140 electrically coupling preselected region 106 to proximal end 94 of probe 92. Pathway 140 is electrically insulated from the exterior of probe 92. Another alternative embodiment of the present invention contemplates pathway 140 being electrically insulated from the interior of probe 92. In such embodiment, pathway 140 may comprise an electrically conductive ribbon embedded in the interior of probe 92.

Instrument 10 further comprises an elongated drive shaft 102 longitudinally disposed within lumen 98 extending from proximal end 94 of probe 92 to at least aperture 100. Shaft 102 is rotatable about the longitudinal axis thereof within lumen 98. Instrument 10 further comprises cutting tool 104 so positioned on shaft 102 opposite aperture 100 as to pass in close proximity thereto during each rotation of shaft 102. Thus, any tissue of the patient urged against the exterior of probe 92 at aperture 100 will be severed. As used herein, the term "severed" includes cutting, grinding, tearing, incising or any other function whereby a portion of tissue is separated from the whole. Energization means for effecting selective electrical coupling of pathway 140 of probe 92 with power source 38 further comprises the invention.

Figure 14:
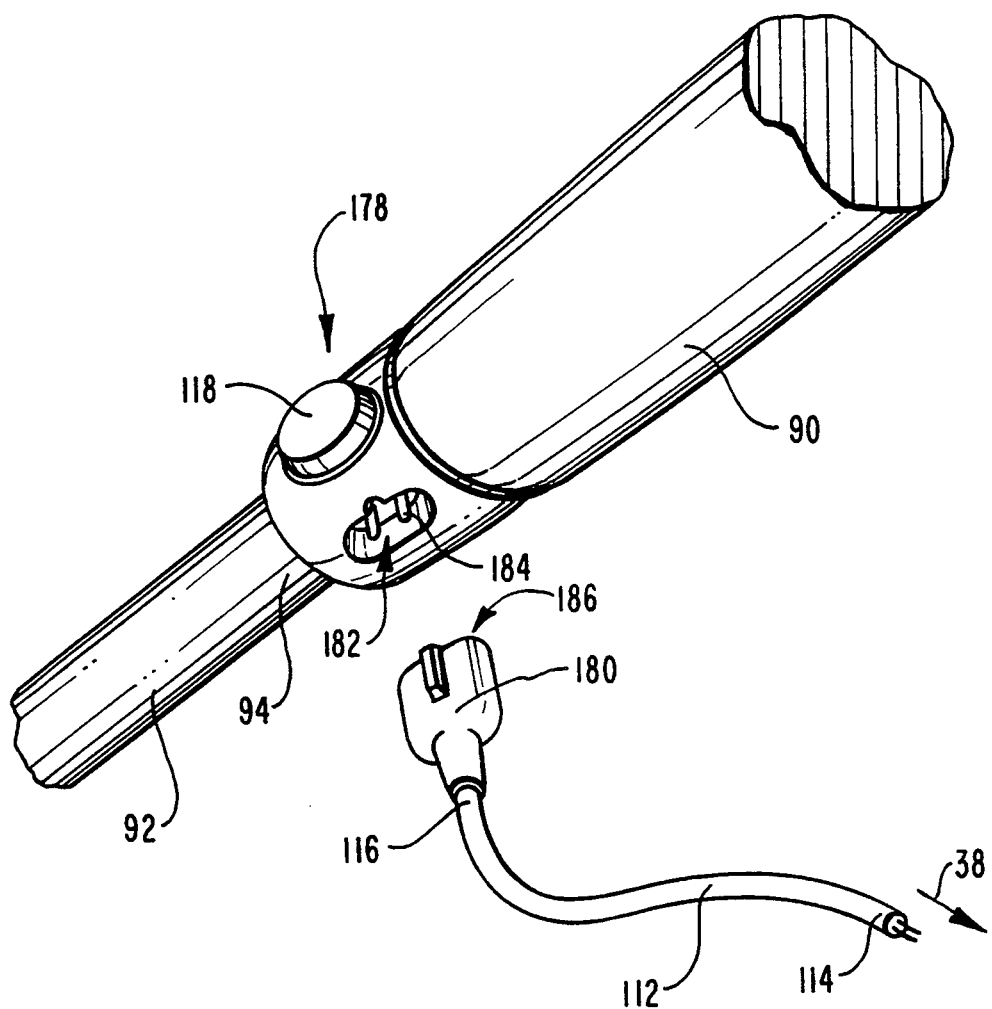
FIG. 14 is a perspective view of the proximal end of an alternative embodiment of an instrument incorporating the teachings of the present invention using the switch that is permanently secured to the probe and a cable that is selectively couplable to the switch.

The invention depicted in FIG. 9 further comprises energization means, by way of example and not limitation, as a cable 112 having a first end 114 and a second end 116. First end 114 is couplable to power source 38. A switch 118, not unlike that depicted in FIG. 14 is secured to proximal end 94 of probe 92. Switch 118 is electrically coupled to second end 116 of cable 112 at one end and electrically coupled to pathway 140 at the other end. Thus, electrical coupling between cable 112 and pathway 140 is selectively effected.

Figure 10:
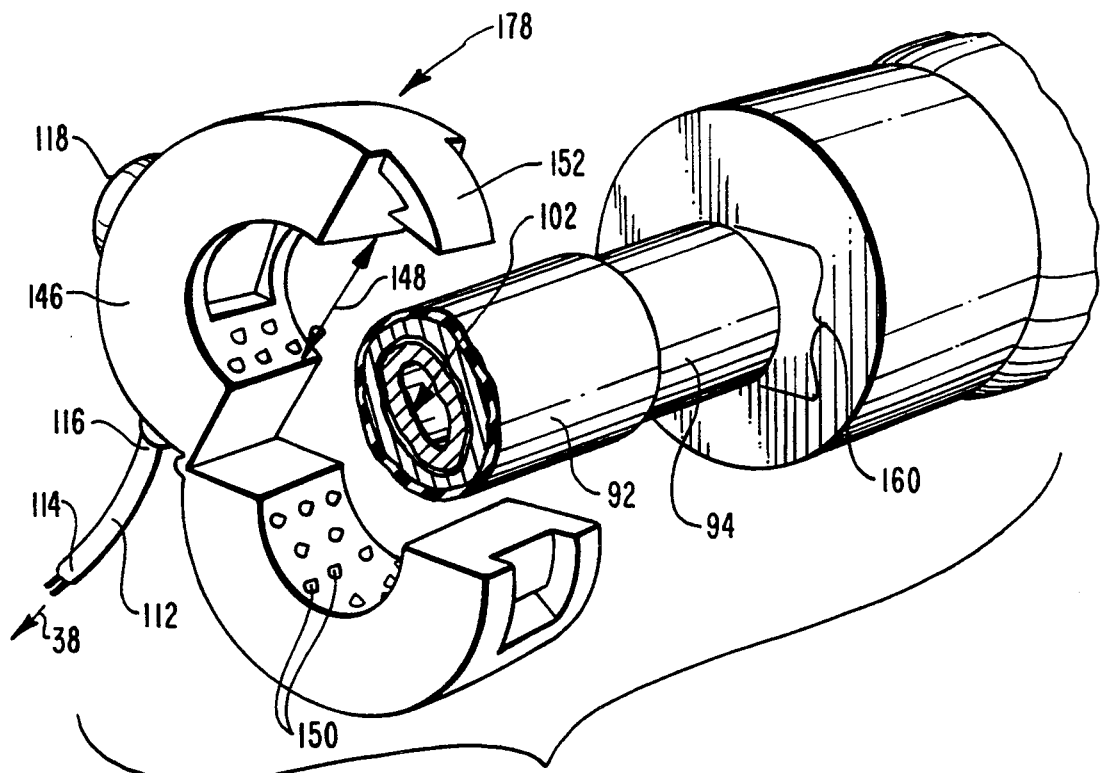
FIG. 10 is a perspective view of the proximal end of an alternative embodiment of an instrument incorporating the teachings of the present invention using a switch couplable to a power source that is selectively detached from the probe of the instrument.

Another alternative embodiment of energization means associated with instrument 10 and incorporating the teachings of the present invention depicted in FIG. 9, by way of example and not limitation, is shown in FIGS. 10 through 14. Such embodiment comprises cable 112 with first end 114 and second end 116. First end 114 is connected to power source 38 and second end 116 is connected to plug 180. Coupler 178 nay be either permanently secured to proximal end 94 of probe 92 as depicted in FIG. 14 or may be selectively secured to proximal end 94 of probe 92, as shown in FIG. 10. As may be seen in FIG. 14, connector 182 is located on coupler 178 and connector 182 is capable of mating with plug 180. By way of example and not limitation, such mating can comprise coordinating male plugs 184 cooperating with female sockets 186 disposed within plug 180.

Other possible methods for mating plug 180 with connector 182 include female sockets positioned within coupler 178 and male plugs positioned on plug 180. Moreover, any other method sufficient to secure plug 180 with coupler 178 is also available so long as plug 180 is sufficiently secured to coupler 178 to avoid inadvertently disconnecting plug 180 from coupler 178. Mating of plug 180 with connector 182 should also be sufficient to allow an effective electrical coupling so that an acceptable level of charge is able to pass from power source 38 to coupler 178 and/or switch 118.

Therefore, energization means may further comprise switch 118 being electrically coupled to connector 182 and switch 118 being selectively electrically couplable to pathway 140 which is depicted in FIG. 9. Switch 118 may further be structured to allow for an open and closed position shown in FIGS. 12-13, by way of example and not limitation, as a closed position coupling pathway 140 to power source 38 and an open position uncoupling pathway 140 from power source 38. Switch 118 is preferably biased in the open position to avoid any unnecessary cauterization during insertion of instrument 10 through instrument portal 16 to surgical site 72 or throughout the procedure.

Figure 11:
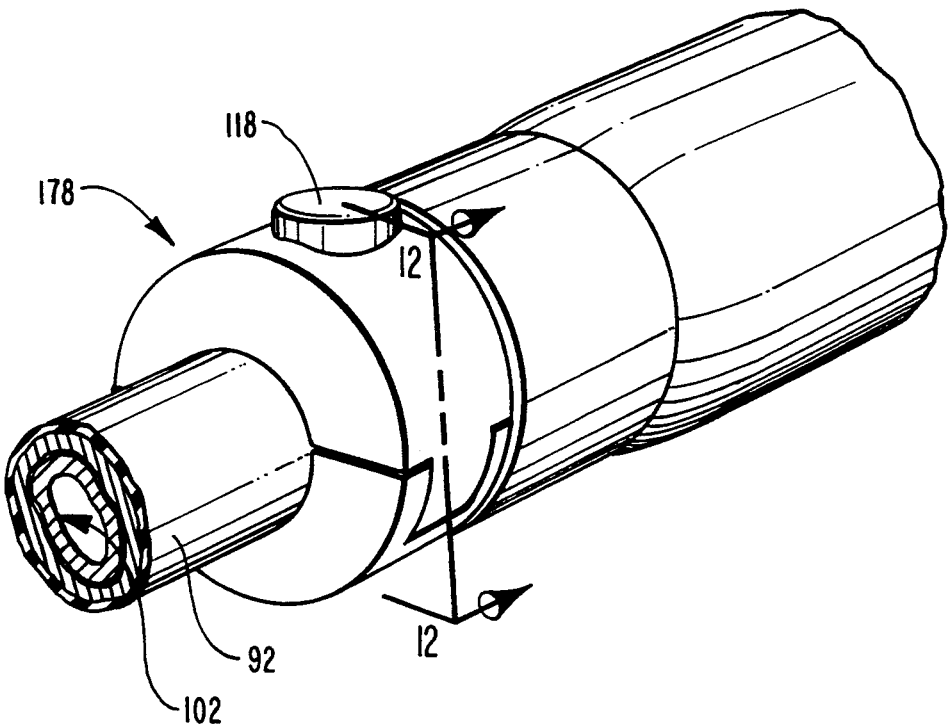
FIG. 11 is a perspective view of the proximal end of the embodiment in FIG. 10 with the switch secured onto the probe.

Energization means depicted in FIG. 14 may also be utilized with other embodiments of instruments incorporating the teachings of the present invention so that coupler 178 may be selectively secured as in FIGS. 10-11 or permanently secured to proximal end 94 of probe 92. Under such embodiments, energization means comprises cable 112 having first end 114 and second end 116, first end 114 being couplable to power source 38 and switch 118 secured to proximal end 94 of probe 92 and being electrically coupled to second end 116 of cable 112. In this structure, electrical coupling is selectively effected between cable 112 and proximal end 94 of probe 92. Selective coupling of coupler 178 is capable of being accomplished as shown, by way of example and not limitation, in FIG. 10, as clasp 146 having an annular inner diameter 148 greater than outer diameter 160 of probe 92. Inner diameter 148 may be further comprised of a retentive surface shown in FIG. 10, by way of example and not limitation, as multiple projections 150 on inner diameter 148. Other methods are available to make inner diameter 148 retentive and are capable of being employed so long as coupler 178 is secured to proximal end 94 of probe 92 without unnecessary slippage.

Clamp 152 on clasp 146 is further provided to affix coupler 178 to probe 92. Electrical pathway 154 shown in FIG. 12 as conductive material is disposed within clasp 146 for coupling electrical power source 38 to switch 118. As further shown in FIG. 12, by way of example and not limitation, switch 118 may be formed so that switch 118 is capable of assuming either an open position as depicted in FIG. 12 in which preselected region 106 is electrically uncoupled from power source 38 or a closed position as depicted in FIG. 13 in which preselected region 106 is electrically coupled to power source 38.

Figure 12:
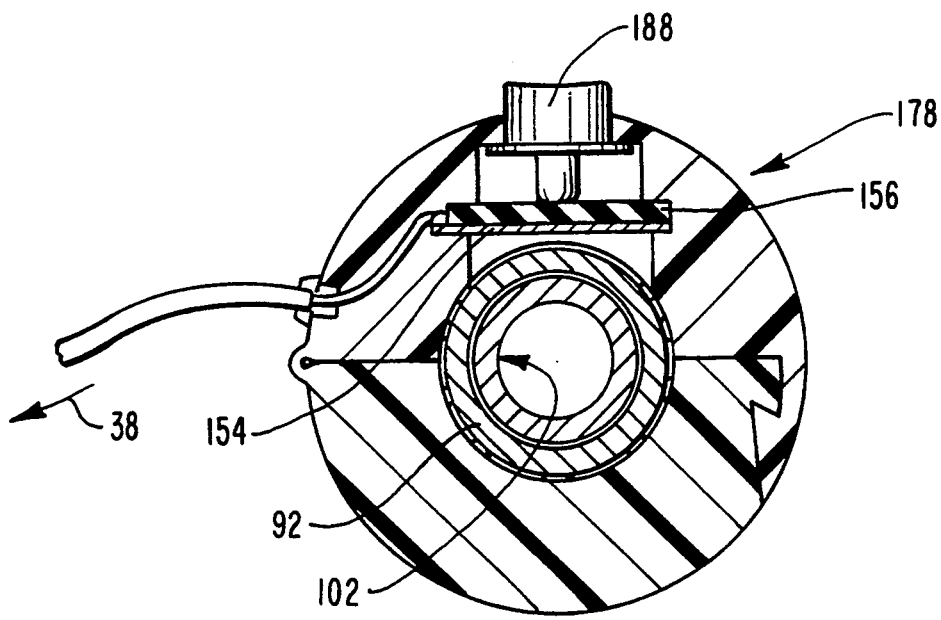
FIG. 12 is a cross-sectional view of the switch taken along line 12—12 in FIG. 11 with the switch in the open position.
Figure 13:
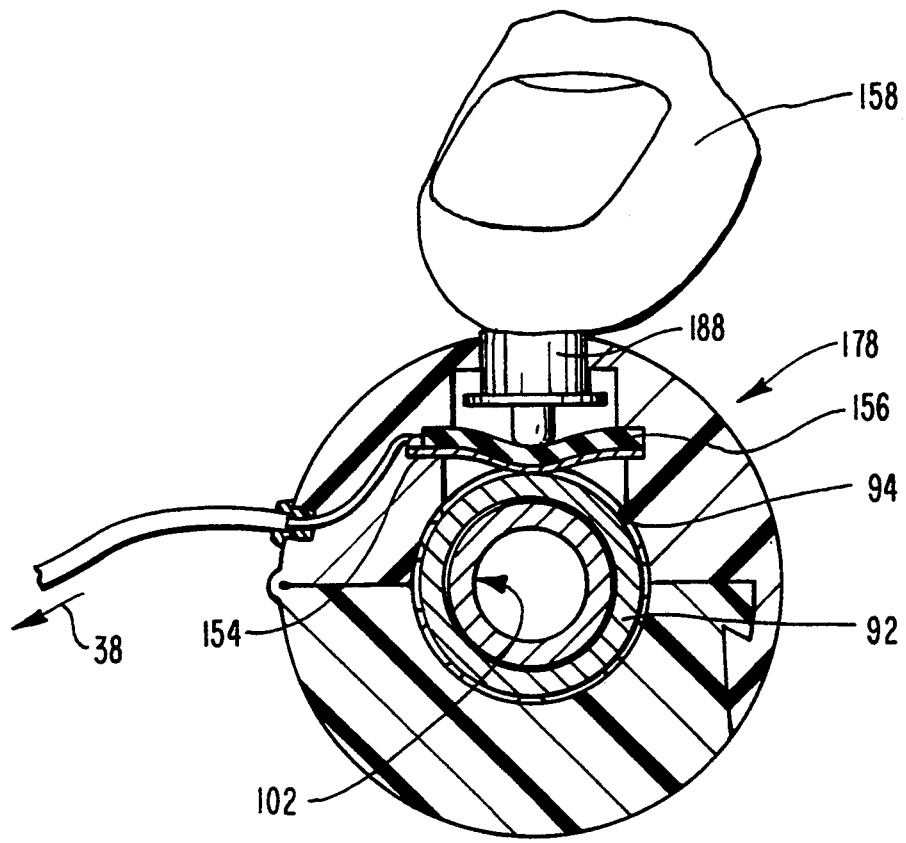
FIG. 13 is a view of the switch in FIG. 12 with the switch in the closed position.

It is preferable that switch 118 be biased into the open position as depicted in FIGS. 12-13. This may be achieved by disposing mechanically resistive material 156 against switch 118. Resistive material 156 is sufficient such that when switch 118 is depressed by finger 158 by placing a force against switch 118 to permit coupling of electrical pathway 154 with proximal end 94 of probe 92 as show in FIG. 13, resistive material 156 will apply an opposing force against switch 118 sufficient to allow switch 118 to rest in the open position as depicted in FIG. 12 when the force placed by finger 158 on switch 118 is removed.

The coupling of power source 38 through switch 118 may also be employed to permit electrical coupling of preselected region 106 by coupling electrical pathway 154 with the structure electrically connecting electrical pathway 154 to preselected region 106 in alternative embodiments of instruments incorporating the teachings of the present invention. By way of example and not limitation, electrical pathway 154 could be structured such that electrical coupling occurs when finger 158 depresses switch 118 with proximal end 94 of probe 92 if proximal end 94 is electrically conductive, as shown in FIG. 4. Alternatively, if probe 92 is nonconductive, coupler 178 may be formed such that electrical pathway 154 is electrically coupled to pathway 140, depicted in FIG. 9.

Figure 15:
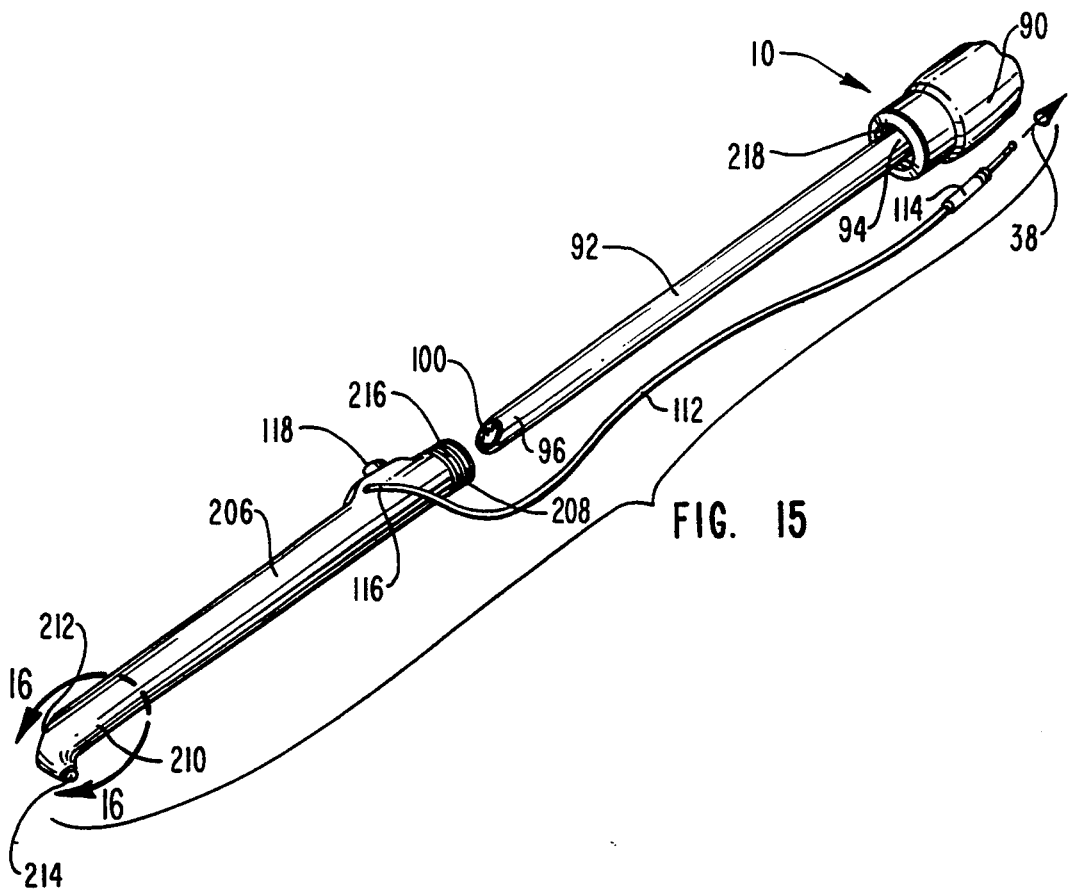
FIG. 15 is an exploded view of an alternative embodiment of an instrument incorporating the teachings of the present invention using an uninsulated electrically conductive probe and an electrically insulative sleeve that is selectively disposable about the exterior of the probe.
Figure 16:
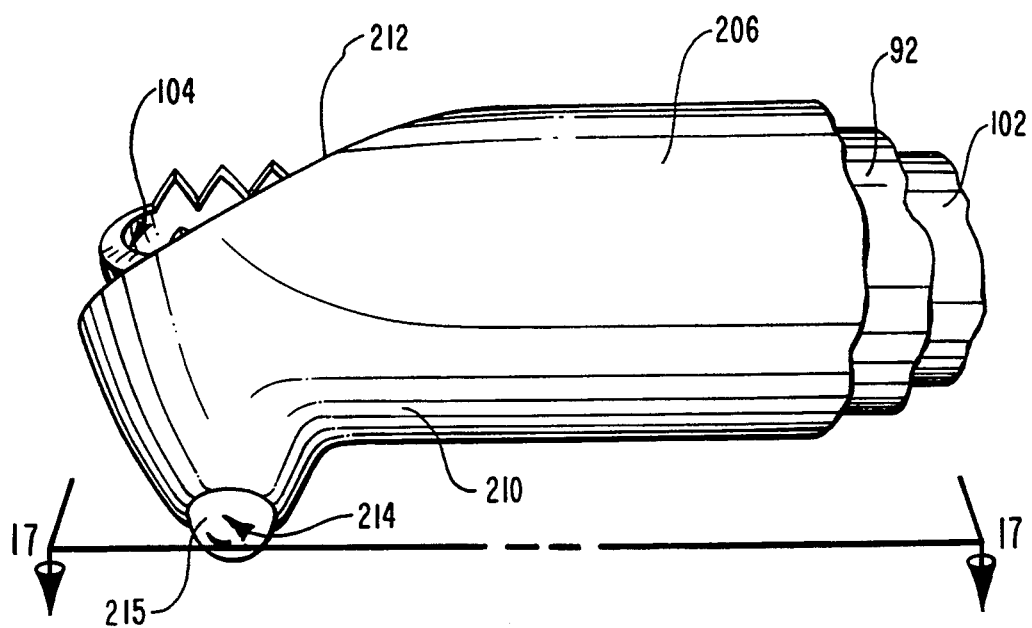
FIG. 16 is an enlarged perspective view of the distal end of the embodiment of the inventive instrument taken along line 16—16 in FIG. 15 with the sleeve assembled on the probe.
Figure 17:
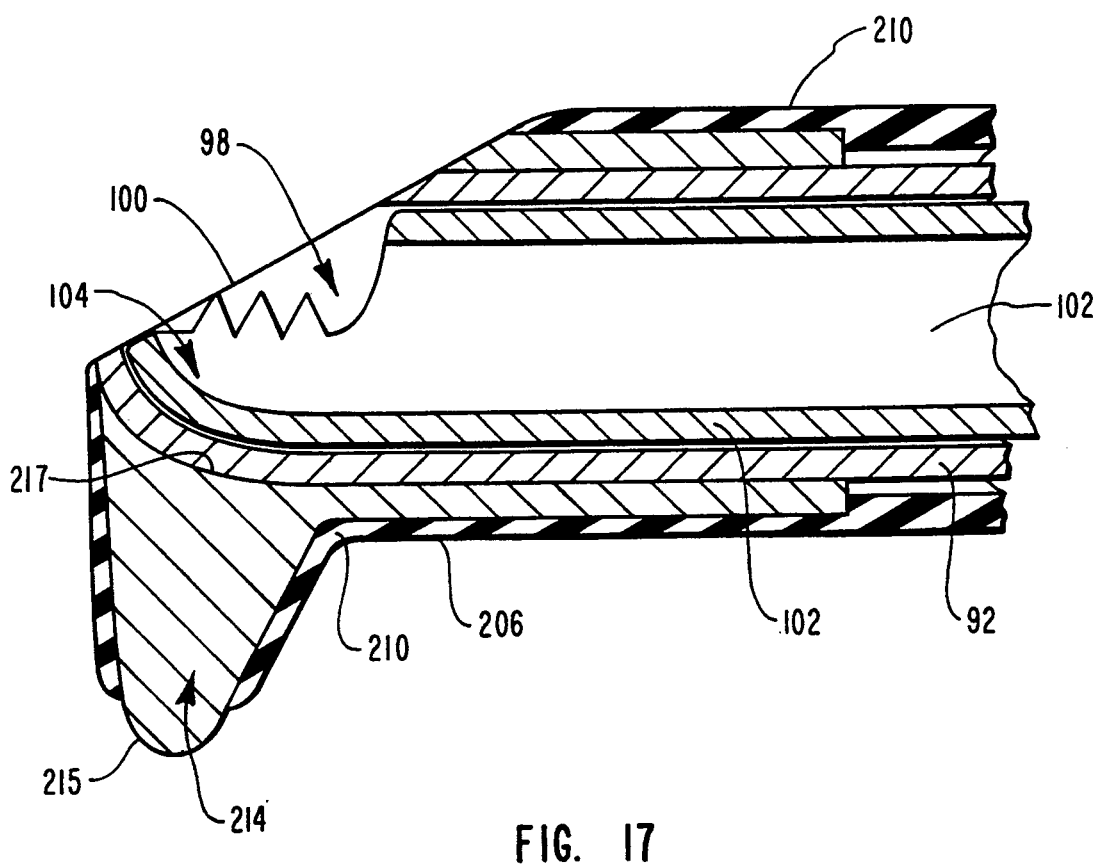
FIG. 17 is a longitudinal cross-sectional view of the embodiment of the inventive instrument taken along line 17—17 in FIG. 16.

In another embodiment shown in FIGS. 15 and 16, an instrument incorporating the teachings of the present invention comprises handle 90 and an elongated electrically conductive probe 92 having a proximal end 94 and a distal end 96. Probe 92 is attached at proximal end 94 to handle 90. As seen in FIG. 17, probe 92 has also formed in the interior thereof a longitudinally extending lumen 98. Lumen 98 is capable of communicating with handle 90.

Distal end 96 of probe 92 has aperture 100 formed through distal end 96 which also permits lumen 98 to communicate with the exterior of probe 92. An elongated drive shaft 102 as depicted in FIG. 17 is longitudinally disposed within lumen 98 and extends from proximal end 94 of probe 92 to at least aperture 100. Shaft 102 is rotatable about the longitudinal axis thereof within lumen 98.

Instrument 10 further comprises cutting tool 104 best shown in FIGS. 16 and 17 so positioned on drive shaft 102 opposite aperture 100 as to pass in close proximity to aperture 100 during each rotation of shaft 102. In this manner, any tissue of the patient urged against the exterior of probe 92 at aperture 100 may be severed.

Instrument 10 is further comprised, as shown in FIGS. 15 and 16, of an electrically insulative sleeve 206. Sleeve 206 is selectively disposable about the exterior of probe 92 extending from proximal end 94 of probe 92 to distal end 96. Sleeve 206 has a first end 208 and a second end 210. First end 208 and second end 210 is so positioned as to be adjacent to proximal end 94 and distal end 96, respectively, of probe 92 when sleeve 206 is disposed about the exterior of probe 92. Second end 210 of sleeve 206 further comprises an aperture 212 formed therethrough. Aperture 212 is positioned on the exterior of probe 92 to permit lumen 98 of probe 92 to communicate with the exterior of sleeve 96. An electrically conductive cauterization contact 214 is located on second end 210 of sleeve 206 having an outer face 215 exposed on the exterior of second end 210 of sleeve 206 and an inner face 217 that engages probe 92 when sleeve 206 is disposed about probe 92.

Instrument 10 further comprises securing means for attaching sleeve 206 at first end 208 to handle 90. By way of example and not limitation, securing means are shown in FIG. 15 as cooperating male threading 216 on first end 208 of sleeve 206 and cooperating female threading 218 disposed in handle 90. Other structures may also be employed to secure sleeve 206 to handle 90. For example, sleeve 206 and handle 90 may be formed to allow for a snap fitting, or the exterior of sleeve 206 may be formed so that a tight union between sleeve 206 and handle 90 is created by a pressure fit. Such other approaches are equally as acceptable as cooperative threading 216 and 218, so long as sleeve 206 is sufficiently secured to handle 90 or placed adjacent to proximal end 94 of probe 92 so that sleeve 206 does not dislodge during the surgical procedure.

Energization means attached to sleeve 206 is further provided for permitting cauterization contact 214 to be selectively electrically coupled with power source 38. By way of example and not limitation, one example of such an energization means is shown in FIG. 15 as switch 118 and cable 112 attached to switch 118 at second end 116 and capable of coupling cable 112 to power source 38 at first end 114. Switch 118 may be formed as already discussed and with a suitable electrical pathway and resistive material as depicted in FIG. 12 to allow power source 38 to be selectively electrically couplable to electrocautery contact 214 in a variety of manners, two examples of which will be discussed below.

As further shown in FIG. 17, one embodiment of energization means usable with sleeve 206 comprises a pathway of electrically conductive material by which switch 118 can electrically couple with proximal end 94 of probe 92 as in FIGS. 12-13. Corresponding, inner face 217 of electrocautery contact 214 is disposed on the interior of sleeve 206 to contact and electrically couple electrocautery contact 214 to probe 92. The interior of second end 210 of sleeve 206 should be formed so that inner face 217 of electrocautery contact 214 is placed adjacent to probe 92 to permit effective electrical coupling.

Figure 18:
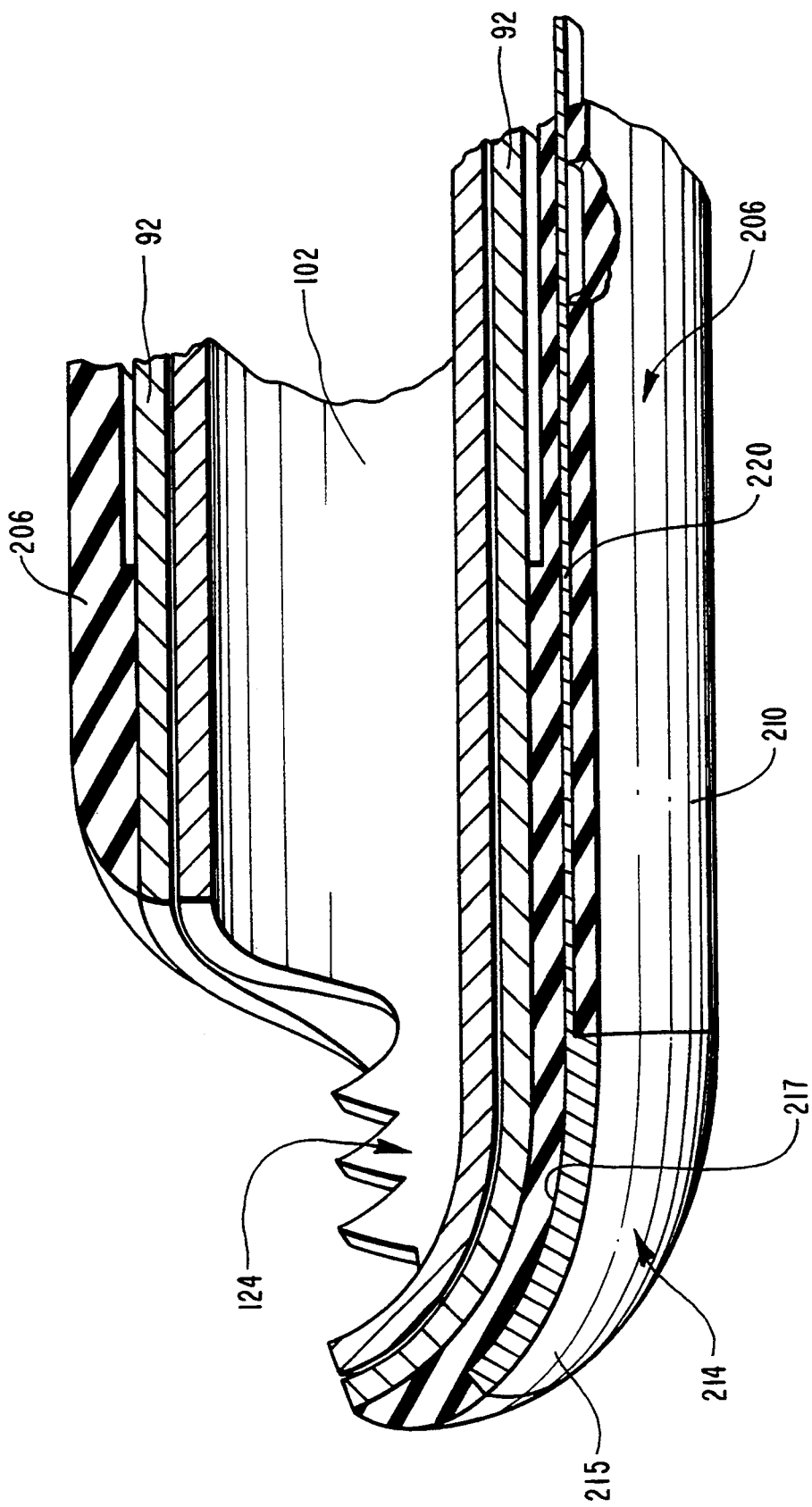
FIG. 18 is a longitudinal cross-sectional view of yet another alternative embodiment of an instrument incorporating the teachings of the present invention with an electrically conductive ribbon embedded in the wall of the sleeve assembled on the probe.

Still another embodiment of the energization means is shown in FIG. 18. Rather than providing for an electrically conductive pathway through conductive probe 92, sleeve 206 can be formed such that electrocautery contact 214 is embedded with inner face 217 thereof insulated by the material of sleeve 206. An electrical pathway 220 is embedded within sleeve 206 thereby electrically insulating pathway 220 from both the exterior and the interior of sleeve 206. Pathway 220 is electrically coupled to electrocautery contact 214 at one end and selectively couplable to switch 118 at another end. In this manner, electrical coupling between cable 112 and electrocautery contact 214 of sleeve 206 may be selectively effected.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An instrument utilizing an electrical power source in a surgical procedure to cut tissue of a patient, said instrument comprising:
   (a) a handle;
   (b) an elongated electrically conductive probe having a proximal end and a distal end and being attached at said proximal end thereof to said handle, said probe having formed in the interior thereof a longitudinally extending lumen communicating with said handle, said distal end of said probe having an aperture formed therethrough permitting said lumen to communicate with the exterior of said probe;
   (c) an elongated drive shaft longitudinally disposed within said lumen extending from said proximal end of said probe to at least said aperture, said drive shaft being rotatably mounted within said lumen of said probe for rotation about the longitudinal axis of said drive shaft;
   (d) a cutting tool positioned on said drive shaft opposite said aperture of said probe, thereby to pass in close proximity to said aperture during each rotation of said shaft and sever any tissue of the patient urged against said exterior of said probe at said aperture; and
   (e) versatility means for selectively electrically cauterizing tissue of the patient contacting a preselected region on said exterior of said distal end of said probe, said versatility means comprising:
      i) an electrically insulative layer disposed on and encircling said exterior of said probe, said layer extending from said proximal end of said probe to the periphery of said preselected region on said exterior of said distal end of said probe; and
      ii) energization means for effecting selective electrical coupling of said probe with the power source.

2. An instrument as recited in claim 1, wherein said versatility means is capable of cutting tissue of the patient.

3. An instrument as recited in claim 1, wherein said versatility means is capable of providing hemostasis in the patient.

4. An instrument as recited in claim 1, wherein said cutting tool comprises a serrated blade.

5. An instrument as recited in claim 1, wherein said cutting tool comprises a burr.

6. An instrument as recited in claim 1, wherein said preselected region comprises the tip of said distal end of said probe.

7. An instrument as recited in claim 1, wherein said preselected region comprises a protuberance projecting from said distal end of said probe in a direction normal to the longitudinal axis thereof, said protuberance having a zip disposed further from the longitudinal axis of said probe than the exterior of said electrically insulative layer.

8. An instrument as recited in claim 1, wherein said electrically insulative layer comprises a heat shrinkable material, in tight engagement with the exterior of said probe.

9. An instrument as recited in claim 1, wherein said electrically insulative layer is adhesively attached to said exterior of said probe.

10. An instrument as recited in claim 1, wherein said electrically insulative layer is applied to the exterior of said probe by immersing said probe in an electrically insulative liquid material.

11. An instrument as recited in claim 1, wherein said energization means comprises:
   (a) a cable having a first end and a second end, said first end being so configured as to be capable of being selectively connected to the power source; and
   (b) a switch secured to said proximal end of said probe, said switch being electrically coupled between said second end of said cable and said proximal end of said probe.

12. An instrument as recited in claim 1, wherein said probe has a substantially circular cross section, and said periphery of said preselected region comprises a circle disposed in a plane substantially perpendicular to the longitudinal axis of said probe.

13. An instrument as recited in claim 1, wherein said energization means comprises:
   (a) a cable having a first end and a second end, said first end being so configured as to be capable of being selectively connected to the power source, said second end being electrically connected to a plug;
   (b) a coupler so configured as to be capable of being selectively secured to said proximal end of said probe;
   (c) an electrical receptacle attached to said coupler, said receptacle being capable of matingly receiving said plug, thereby to electrically couple said receptacle with said cable; and
   (d) a switch electrically coupled between said receptacle and said proximal end of said probe, when said coupler is secured to said proximal end of said probe, said switch being capable of selectively assuming either:
      i) a closed position in which said probe is electrically coupled to the power source when said coupler is secured to said proximal end of said probe, said plug is matingly received by said receptacle, and said first end of said cable is connected to the power source; or
      ii) an open position in which said probe is electrically uncoupled from the power source, even when said coupler is secured to said proximal end of said probe, said plug is matingly received by said receptacle, and said first end of said cable is connected to the power source, said switch being biased into said open position thereof.

14. An instrument utilizing an electrical power source in a surgical procedure to cut tissue of a patient, said instrument comprising:
   (a) a handle;
   (b) an elongated electrically conductive probe having a proximal end and a distal end and being attached at said proximal end thereof to said handle, said probe having formed in the interior thereof a longitudinally extending lumen communicating with said handle, said distal end of said probe having an aperture formed therethrough permitting said lumen to communicate with the exterior of said probe;

(c) an elongated drive shaft longitudinally disposed within said lumen extending from said proximal end of said probe to at least said aperture, said drive shaft being rotatably mounted within said lumen of said probe for rotation about the longitudinal axis of said drive shaft;

(d) a cutting tool positioned on said drive shaft opposite said aperture of said probe, thereby to pass in close proximity to said aperture during each rotation of said shaft and sever any tissue of the patient urged against said exterior of said probe at said aperture; and (e) versatility means for selectively electrically cauterizing tissue of the patient contacting a preselected region on said exterior of said distal end of said probe, said preselected region comprising a protuberance projecting from said distal end of said probe.

15. An instrument as recited in claim 14, wherein said protuberance projects from said distal end in a direction normal to the longitudinal axis of said probe.

16. An instrument utilizing an electrical power source employed in a surgical procedure to cut tissue of a patient, said instrument comprising:

(a) a handle;

(b) an elongated electrically conductive probe having a proximal end and a distal end and being attached at said proximal end thereof to said handle, said probe having formed in the interior thereof a longitudinally extending lumen communicating with said handle, said distal end of said probe having an aperture formed therethrough permitting said lumen to communicate with the exterior of said probe;

(c) an elongated drive shaft longitudinally disposed within said lumen extending from said proximal end of said probe to at least said aperture, said drive shaft being rotatably mounted within said lumen of said probe for rotation about the longitudinal axis of said drive shaft;

(d) a cutting tool positioned on said shaft opposite said aperture of said probe, thereby to pass in close proximity to said aperture during each rotation of said shaft and sever any tissue of the patient urged against said exterior of said probe at said aperture;

(e) an electrically insulative layer disposed on and encircling the exterior of said probe, said layer extending from said proximal end of said probe to the periphery of a preselected region on said exterior of said distal end of said probe; and (f) a switch electrically coupled between the power source and said proximal end of said probe, said switch being capable of selectively assuming either a closed position in which said probe is electrically coupled to the power source, or an open position in which said probe is electrically uncoupled from the power source, thereby in said closed position of said switch allowing said preselected region on said distal end of said probe to be capable of selectively cauterizing tissue of the patient contacting said preselected region.

17. An instrument as recited in claim 16, wherein said preselected region comprises the tip of said distal end of said probe.

18. An instrument as recited in claim 16, wherein said preselected region comprises a protuberance projecting from said distal end of said probe.

19. An instrument as recited in claim 18, wherein said protuberance projects from said distal end in a direction normal to the longitudinal axis of said probe.

20. An instrument as recited in claim 16, wherein said preselected region comprises a protuberance having a tip disposed further from the longitudinal axis of said probe than the exterior of said electrically insulative layer.

21. An instrument as recited in claim 16, wherein said electrically insulative layer comprises a heat shrinkable material in tight engagement with the exterior of said probe.

22. An instrument as recited in claim 16, wherein said electrically insulative layer is adhesively attached to said exterior of said probe.

23. An instrument as recited in claim 16, wherein said electrically insulative layer is applied to the exterior of said probe by immersing said probe in an electrically insulative liquid material.

24. An instrument as recited in claim 16, wherein said electrically insulative layer is formed into a beveled edge at said periphery of said preselected region.

25. An instrument as recited in claim 16, further comprising coupler means for selectively securing said switch to said proximal end of said probe, said coupler means comprising:

(a) a hinged clasp having an inner surface corresponding in shape to the outer surface of said probe at a location thereon proximal of said insulative layer, said switch being mounted to said clasp; and (h) an electrical pathway disposed within said clasp for coupling the electrical power source to said switch.

26. An instrument as recited in claim 16, wherein said switch is biased into said open position thereof.

27. An instrument utilizing an electrical power source in a surgical procedure to cut tissue of a patient, said instrument comprising:

(a) a handle;

(b) an elongated probe formed of an electrically insulative material, said probe having a proximal end and a distal end and being attached at said proximal end thereof to said handle, said probe having formed in the interior thereof a longitudinally extending lumen communicating with said handle, said distal end of said probe having an aperture formed therethrough between said lumen and the exterior of said probe, said probe further comprising:

i) an electrically conductive preselected region located on the exterior of said distal end of said probe; and ii) conductive means for electrically coupling said preselected region to said proximal end of said probe, said conductive means being embedded in said electrically insulative material of said probe, thereby being electrically insulated at least from said exterior of said probe;

(c) an elongated drive shaft longitudinally disposed within said lumen extending from said proximal end of said probe to at least said aperture, said drive shaft being rotatably mounted within said lumen of said probe for rotation about the longitudinal axis of said drive shaft;

(d) a cutting tool positioned on said drive shaft opposite said aperture of said probe, thereby to pass in close proximity to said aperture during each rotation of said drive shaft and sever any tissue of the patient urged against said exterior of said probe at said aperture; and (e) energization means for effecting selective electrical coupling of said conductive means at said proximal end of said probe with the power source.

28. An instrument as recited in claim 27, wherein said conductive means is electrically insulated from said interior of said probe.

29. An instrument as recited in claim 28, wherein said conductive means comprises an electrically conductive ribbon embedded in the wall of said probe.

30. An instrument as recited in claim 27, wherein said preselected region comprises a protuberance projecting from said distal end of said probe.

31. An instrument as recited in claim 30, wherein said protuberance projects from said distal end of said probe in a direction normal to the longitudinal axis of said probe.

32. An instrument as recited in claim 30, wherein said protuberance comprises a tip disposed further from the longitudinal axis of said probe than the exterior of said probe.

33. An instrument as recited in claim 27, wherein said energization means comprises:
(a) a cable having a first end and a second end, said first end being so configured as to be capable of being selectively connected to the power source; and
(b) a switch secured to said proximal end of said probe and being electrically coupled between said second end of said cable and said conductive means at said proximal end of said probe, said switch being capable of selectively assuming either a closed position in which said conductive means is electrically uncoupled from said second end of said cable, or an open position in which said conductive means is electrically uncoupled second end of said cable, thereby to selectively effect electrical coupling between said cable and said conductive means.

34. An instrument as recited in claim 27, wherein said energization means comprises:
(a) a cable having a first end and a second end, said first end being so configured as to be capable of being selectively connected to the power source, said second end being electrically connected to a plug;
(b) a hub secured to said proximal end of said probe;
(c) an electrical receptacle attached to said hub, said receptacle being capable of matingly receiving said plug, thereby to electrically couple said receptacle with said cable; and
(d) a switch on said hub electrically coupled between said receptacle and said conductive means at said proximal end of said probe, said switch being capable of selectively assuming either:
i) a closed position in which said conductive means at said proximal end of said probe is electrically coupled to the power source, when said matingly received by said receptacle and said first end of said cable is connected to or
ii) an open position in which said conductive means is electrically uncoupled from the power source, even when said plug is matingly received by said receptacle and said first end of said cable is connected to said power source, said switch being biased in said open position thereof.

35. An instrument utilizing an electrical power source in a surgical procedure to cut tissue of a patient, said instrument comprising:
(a) a handle;
(b) an elongated electrically conductive probe having a proximal end and a distal end and being attached at said proximal end thereof to said handle, said probe having formed in the interior thereof a longitudinally extending lumen communicating with said handle, said distal end of said probe having a first aperture formed therethrough between said lumen and the exterior of said probe;
(c) an elongated drive shaft longitudinally disposed within said lumen extending from said proximal end of said probe to at least said aperture, said shaft being rotatably mounted within said lumen of said probe for rotation about the longitudinal axis of said drive shaft;
(d) a cutting tool positioned on said drive shaft opposite said aperture of said probe, thereby to pass in close proximity to said aperture during each rotation of said drive shaft and sever any tissue of the patient urged against said exterior of said probe at said aperture;
(e) an electrically insulative sleeve having a first end and a second end, said insulative sleeve being selectively disposable about said exterior of said probe with said first end thereof adjacent to said proximal end of said probe and said second end thereof adjacent to said distal end of said probe, said insulative sleeve having a second aperture formed through said second end thereof at a position adjacent to said first aperture of said probe when said insulative sleeve is disposed about said exterior of said probe, thereby to permit said lumen of said probe to communicate with the exterior of said sleeve through said adjacent first and second apertures;
(f) an electrically conductive electrocautery contact attached to said second end of said insulative sleeve, said electrocautery contact having an inner and an outer face, and said outer face of said electrocautery contact be exposed on the exterior of said second end of said insulative sleeve;
(g) securing means for attaching said insulative sleeve at said first end thereof to said handle; and
(h) energization means attached to said sleeve for permitting said electrocautery contact to be selectively electrically coupled with the power source.

36. An instrument as recited in claim 35, wherein said preselected region comprises a protuberance projecting from said second end of said sleeve.

37. An instrument as recited in claim 36, wherein said protuberance projects from said second end of said sleeve in a direction normal to the longitudinal axis of said probe.

38. An instrument as recited in claim 35, wherein a portion of said exterior face of said electrocautery contact is disposed further from the longitudinal axis of said probe than is the exterior of said sleeve.

39. An instrument as recited in claim 35, wherein said inner face of said electrocautery contact effects electrical contact with said exterior of said insulative sleeve is disposed about said probe, and said energization means comprises:
(a) a cable having a first end and a second end, said first end being so configured as to be capable of being selectively connected to the power source; and (b) a switch secured to said first end of said sleeve, electrically coupled between said second end of said cable and said exterior of said proximal end of said probe when said insulative sleeve is disposed about said probe.

40. An instrument as recited in claim 39, wherein said switch is capable of assuming either an open position in which said probe is electrically uncoupled from the power source when said insulative sleeve is disposed about said probe, or a closed position in which said probe is electrically coupled to the power source when said insulative sleeve is disposed about said probe, said switch being biased into said open position thereof.

41. An instrument as recited in claim 35, wherein said energization means comprises:
    (a) a cable having a first end and a second end, said first end being so configured as to be capable of being electrically connected to the power source;
    (b) conductive means for electrically coupling said electrocautery contact to said first end of said insulative sleeve, said conductive means being the wall of said insulative sleeve; and
    (c) a switch secured to said first end of said sleeve electrically coupled between said second end of said cable and said conductive means at said first end of said insulative sleeve.

42. An instrument as recited in claim 41, wherein said switch is capable of assuming either an open position in which said conductive means is electrically uncoupled from the power source when said first end of said cable is connected thereto, or a closed position in which said conductive means is electrically coupled to the power source when said first end of said cable is connected thereto, said switch being biased into said open position thereof.

43. A method for conducting a surgical procedure to cut tissue of a patient located at a surgical site interior to the body thereof, while electrically controlling bleeding at the surgical site, said method comprising the steps:
    (a) forming an access passageway from the exterior of the body of the patient to the surgical site;
    (b) advancing through said access passageway to the surgical site the distal tip of a surgical instrument, said instrument comprising:
       i) a handle;
       ii) an elongated electrically conductive probe having a proximal end and a distal end and being attached at said proximal end thereof to said handle, said probe having formed in the interior thereof a longitudinally extending lumen communicating with said handle, said distal end of said probe having a first aperture formed therethrough between said lumen and the exterior of said probe;
       iii) an elongated drive shaft longitudinally disposed within said lumen extending from said handle to said aperture, said drive shaft being rotatably mounted within said lumen of said probe for rotation about the longitudinal axis of said drive shaft; and
       iv) a cutting tool positioned on said drive shaft opposite said aperture;
    (c) electrically insulating the exterior of said probe from said proximal end thereof to the periphery of a preselected region on said exterior of said distal end of said probe, said step of insulating occurring prior to said step of advancing;
    (d) visually observing the surgical site during use of said instrument to cut tissue of the patient thereat;
    (e) electrically coupling an electrical power source to said proximal end of said probe when bleeding at the surgical site is detected in said step of visually observing, thereby allowing said preselected region on said exterior of said distal end of said probe to cauterize tissue of the patient contacted thereby; and
    (f) terminating said step of electrically coupling when said step of visually observing discloses that bleeding at the surgical site has been curtailed by cauterizing of tissue of the patient in said step of electrically coupling.

44. A method as recited in claim 43, wherein said step of electrically insulating comprises the steps:
    (a) sliding an electrically insulative heat-shrinkable cylinder onto the exterior of said probe and into abutment with said handle, said electrically insulative layer being so configured to extend from said handle to said periphery of said preselected region on said exterior of said distal end of said probe; and
    (b) heating said sleeve, thereby to shrink said sleeve into tight engagement with said exterior of said probe.

45. A method as recited in claim 43, wherein said step of electrically insulating comprises the steps:
    (a) masking said preselected region on said exterior of said probe;
    (b) closing said aperture formed through said distal end of said probe;
    (c) immersing the exterior of said probe into a liquified electrically insulative material; and
    (d) curing said insulative material.

46. A method as recited in claim 43, wherein said step of electrically insulating comprises the step of applying a polymeric electrically insulative coating to the exterior of said probe from said proximal end thereof to said periphery of said preselected region.

47. A method as recited in claim 43, wherein said step of electrically insulating comprises the step of advancing an electrically insulative sleeve onto said exterior of said probe, said sleeve extending from said proximal end thereof to said aperture and said periphery of said prescribed region of said distal end of said probe.

48. A method as recited in claim 47, wherein said step of electrically insulating further comprises the step of applying adhesive between said electrically insulative sleeve and said exterior of said probe.

49. A method as recited in claim 43, wherein said step of electrically coupling comprises the steps:
    (a) securing to said proximal end of said probe a switch having a first side thereof electrically coupled to said probe;
    (b) electrically coupling a conductive cable between a second side of said switch and the power source; and
    (c) selectively operating said switch.

50. A method for conducting a surgical procedure to cut tissue of a patient located at a surgical site interior to the body thereof, while selectively controlling bleeding at the surgical site, said method comprising the steps:
    (a) forming an access passageway from the exterior of the body of the patient to the surgical site;
    (b) advancing through said access passageway to the surgical site the distal tip of a surgical instrument, said instrument comprising:
       i) a handle;

ii) an elongated electrically conductive probe having a proximal end and a distal end and being attached at said proximal end thereof to said handle, said probe having formed in the interior thereof a longitudinally extending lumen communicating with said handle, said distal end of said probe having an aperture formed therethrough between said lumen and the exterior of said probe;

iii) an elongated drive shaft longitudinally disposed within said lumen extending from said proximal end of said probe to said aperture, said drive shaft being rotatably mounted within said lumen of said probe for rotation about the longitudinal axis of said drive shaft; and iv) a cutting tool positioned on said drive shaft opposite said aperture;

(c) sliding an electrically insulative sleeve; onto the exterior of said probe before the step of advancing, said electrically insulative sleeve having a first end and a second end, and said step of sliding bringing said first end of said insulative sleeve into abutment with said handle, said insulative sleeve further comprising:

i) an electrically conductive preselected region on the exterior of said second end of said sleeve;

ii) conductive means for electrically coupling said preselected region to said first end of said insulated sleeve, said conductive means being embedded in the wall of said insulative sleeve; and iii) a second aperture formed through said second end of said sleeve.

(d) aligning said second aperture with said first aperture thereby to permit said lumen of said probe to communicate with the exterior of said sleeve through said first and second Apertures combined;

(e) securing said sleeve at said first end thereof to said handle;

(f) visually observing the surgical site during use of said instrument to cut tissue of the patient thereat;

(g) electrically coupling an electrical power source to said conductive means at said first end of said insulative sleeve when bleeding at the surgical site detected in said step of visually observing, thereby allowing said preselected region on the exterior of said second end of said sleeve to cauterize tissue of patient contacted thereby; and (h) terminating said step of electrically coupling when said step of visually observing discloses the bleeding in the surgical site has been curtailed by cauterizing of tissue of the patient in said stem of electrically coupling.

51. A method as recited in claim 50, wherein said step of securing said sleeve at said first end thereof to, said handle comprises the steps:

(a) providing each of said first end of said insulating sleeve and said handle with respective cooperating threads;

(b) engaging said threads of said handle with said threads on said first end of said sleeve in said step of sliding; and (c) rotating said sleeve until said first end of said sleeve is secured to said handle with said first aperture aligned with said second aperture.

52. A method as recited in claim 50, wherein said step of electrically coupling comprises the steps:

(a) securing to said first end of said sleeve a switch having a first side thereof electrically coupled to said conductive means;

(b) electrically coupling a conductive cable between a second side of said switch and the power source; and (c) selectively operating said switch.

53. A method for conducting a surgical procedure to cut tissue of a patient located at the surgical site interior to the body thereof, while electrically controlling bleeding at the surgical site, said method comprising the steps:

(a) forming an access passageway from the exterior of the body of the patient to the surgical site;

(b) advancing through said access passageway to the surgical site the distal tip of a surgical instrument, said instrument comprising:

i) a handle;

ii) an elongated probe formed of an electrically insulative material, said probe having a proximal end and a distal end and being attached at said proximal end thereof to said handle, said probe having formed in the interior thereof a longitudinally extended lumen communicating with said handle, said distal end of said probe having an aperture formed therethrough between said lumen and the exterior of said probe;

iii) an electrically conductive preselected region located on the exterior of said distal end of said probe;

iv) conductive means for electrically coupling said preselected region to said proximal end of said probe;

v) an elongated drive shaft longitudinally disposed within said lumen extending from said proximal end of said probe to at least said aperture, said drive shaft being rotatably mounted within said lumen of said probe for rotation about the longitudinal axis of said drive shaft; and vi) a cutting tool positioned on said drive shaft opposite said aperture of said probe;

(c) electrically insulating said conductive means from said preselected region to said proximal end of said probe, said step of insulating occurring prior to said step of advancing;

(d) visually observing the surgical site during use of said instrument to cut tissue of the patient thereat;

(e) electrically coupling an electrical power source to said conductive mean at said proximal end of said probe when bleeding at the surgical site is detected in said step of visually observing, thereby allowing said preselected region on said exterior of said distal end of said probe to cauterize tissue of the patient contacted thereby; and (f) terminating said step of electrically coupling when said step of visually observing discloses that bleeding at the surgical site has been curtailed by cauterizing of tissue of the patient in said step of electrically coupling.

* * * * *

UNITED STATES PATENT AND TRADEMARK OFFICE
CERTIFICATE OF CORRECTION

PATENT NO. : 5,364,395
DATED : November 15, 1994
INVENTOR(S) : HUGH S. WEST, Jr.

It is certified that error appears in the above-indentified patent and that said Letters Patent is hereby corrected as shown below:

Title page, column 1, line 20, where "Attorney, Agent, or Firm" is listed, "Hydegger" should be --Nydegger--
    Column 2, line 60, "to:31" should be --tool--
    Column 5, line 33, delete "conductive"
    Column 12, line 8, "nay" should be --may--
    Column 14, line 40, delete "further"
    Column 18, line 31, "(h)" should be --(b)--
    Column 19, line 37, after "uncoupled" insert --from said--
    Column 19, line 59, after "said" insert --plug is--
    Column 19, line 61, after "to" insert --said power source;--
    Column 20, line 50, "preselected region" should be --electrocautery contact--
    Column 20, line 62, after "said" insert --probe, when said--(2nd occur:
    Column 21, line 21, after "being" insert --embedded in--
    Column 23, line 18, delete ";"
    Column 23, line 36, "Apertures" should be --apertures--
    Column 23, line 44, before "detected" insert --is--
    Column 23, line 46, after "tissue of" insert --the--
    Column 23, line 51, "stem" should be --step--
    Column 23, line 54, delete ","

Signed and Sealed this

Twentieth Day of June, 1995

*Attest:*

BRUCE LEHMAN

*Attesting Officer*     *Commissioner of Patents and Trademarks*